(12) United States Patent
Fotheringham et al.

(10) Patent No.: US 8,557,558 B2
(45) Date of Patent: Oct. 15, 2013

(54) COMPOSITIONS AND METHODS OF PRODUCING ENTEROKINASE IN YEAST

(75) Inventors: Ian Fotheringham, Edinburgh (GB); Peter Sheffield, Vista, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/303,691

(22) Filed: Nov. 23, 2011

(65) Prior Publication Data

US 2012/0156720 A1 Jun. 21, 2012

Related U.S. Application Data

(60) Provisional application No. 61/416,622, filed on Nov. 23, 2010.

(51) Int. Cl.
*C12N 9/50* (2006.01)
*C12N 9/64* (2006.01)
*C12N 1/00* (2006.01)
*C12N 15/00* (2006.01)
*C07H 21/04* (2006.01)

(52) U.S. Cl.
USPC ..... 435/219; 435/226; 435/320.1; 435/254.2; 536/23.2; 536/23.4

(58) Field of Classification Search
None
See application file for complete search history.

(56) References Cited

U.S. PATENT DOCUMENTS 6,746,859 B1 6/2004 LaVallie
2011/0111483 A1* 5/2011 Steward et al. .......... 435/252.33

FOREIGN PATENT DOCUMENTS

WO 2008-0136014 11/2008

OTHER PUBLICATIONS

LaVallie et al., "Cloning and Functional Expression of a cDNA Encoding the Catalytic Subunit of Bovine Enterokinase", J. Biol. Chem. 268:23311-23317, 1993.*
Claes Gustafsson, et al., Jul. 2004, Condon Bias and Heterologous Protein Expression, Trends in Biotechnology, 22 (7), 346-353.
Gang Wu, 2006, The Synthetic Gene Designer: A Flexible Web Platform to Explore Sequence Manipulation For Heterologous Expression, Protein Expression and Purification, 47, 441-445.
Laura Vozza, Jan. 14, 1996, Production of a Recombinant Bovine Enterokinase Catalytic Subunit in the Methylotrophic Yeast, Bio/Technology, 14, 77-81.
Lisheng Peng, 2004, High-Level Secretory Production of Recombinant Bovine Enterokinase Light Chain by Pichia Pastoris, Journal of Biotechnology, 108, 185-192.
Rachel Daly, 2005, Expression of Heterologous Proteins in Pichia Pastoris: a Useful Experimental Tool in Protein Engineering and Production, Journal of Molecular Recognition, 18, 119-138.
Seong Choi, Dec. 20, 2001, Recombinant Enterokinase Light Chain With Affinity Tag: Expression From *Saccharomyces cerevisiae* and Its Utilities in Fusion Protein Technology, Biotechnology and Bioengineering, 75 (6), 719-724.
Yasunori Kitamoto, 1994, Enterokinase, The Initiator of Intestinal Digestion, is a Mosaic Protease Composed of a Distinctive Assortment of Domains, Proc. Natl. Acad. Sci., 91, 7588-7592.
ZJ Fang, Jun. 11, 2009, The Expression of Bovine Enterokinase Catalytic Subunit in Methylotropic Yeast *Pichia pastoris*, Bioinformatics and Biomedical Engineering pp. 1-3, 3rd International Conference.

* cited by examiner

*Primary Examiner* — David J Steadman
(74) *Attorney, Agent, or Firm* — Kenton Abel; Debra Condino

(57) ABSTRACT

The present specification disclose polynucleotide molecules encoding an enterokinase, yeast expression constructs including a yeast expression vector and a polynucleotide molecules encoding an enterokinase, yeast cells comprising such a yeast expression construct, methods of producing enterokinase using such yeast cells, and method of cleaving or preparing a recombinant polypeptide using an enterokinase produced by such methods.

14 Claims, 1 Drawing Sheet

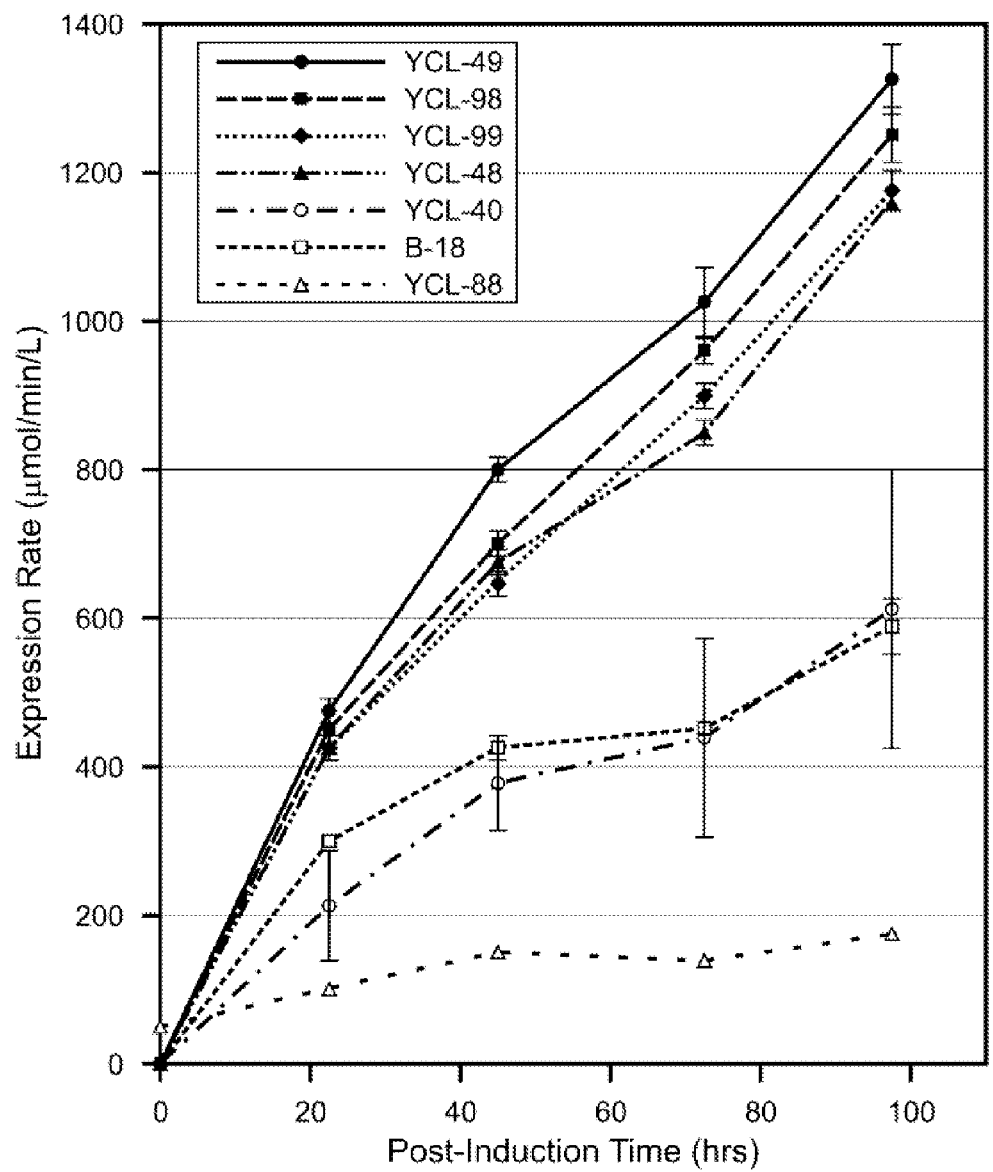

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: Cleavage site for enterokinase

<400> SEQUENCE: 1

Asp Asp Asp Asp Lys
1               5
```

<210> SEQ ID NO 2
<211> LENGTH: 708
<212> TYPE: DNA
<213> ORGANISM: Bos taurus

<400> SEQUENCE: 2

```
attgtcggag gaagtgactc cagagaagga gcctggcctt gggtcgttgc tctgtatttc     60
gacgatcaac aggtctgcgg agcttctctg gtgagcaggg attggctggt gtcggccgcc    120
cactgcgtgt acgggagaaa tatggagccg tctaagtgga aagcagtgct aggcctgcat    180
atggcatcaa atctgacttc tcctcagata gaaactaggt tgattgacca aattgtcata    240
aacccacact acaataaacg gagaaaggac aatgacatcg ccatgatgca tcttgaaatg    300
aaagtgaact acacagatta tatacagcct atttgtttac cagaagaaaa tcaagttttt    360
tccccaggaa gaatttgttc tattgctggc tgggggacac ttatatatca aggttctact    420
gcagacgtac tgcaagaagc tgacgttccc cttctatcaa atgagaaatg tcaacaacag    480
atgccagaat ataacattac ggaaaatatg gtgtgtgcag gctacgaagc aggaggggta    540
gattcttgtc aggggattc aggcggacca ctcatgtgcc aagaaaacaa cagatggctc    600
ctggctggtg tgacatcatt tggatatcag tgtgcactgc ctaatcgccc aggggtgtat    660
gcccgggtcc caaggttcac agagtggata caaagttttc tacattag                 708
```

<210> SEQ ID NO 3
<211> LENGTH: 235
<212> TYPE: PRT
<213> ORGANISM: Bos taurus

<400> SEQUENCE: 3

```
Ile Val Gly Gly Ser Asp Ser Arg Glu Gly Ala Trp Pro Trp Val Val
  1               5                  10                  15

Ala Leu Tyr Phe Asp Asp Gln Gln Val Cys Gly Ala Ser Leu Val Ser
             20                  25                  30

Arg Asp Trp Leu Val Ser Ala Ala His Cys Val Tyr Gly Arg Asn Met
         35                  40                  45

Glu Pro Ser Lys Trp Lys Ala Val Leu Gly Leu His Met Ala Ser Asn
     50                  55                  60

Leu Thr Ser Pro Gln Ile Glu Thr Arg Leu Ile Asp Gln Ile Val Ile
 65                  70                  75                  80

Asn Pro His Tyr Asn Lys Arg Arg Lys Asn Asn Asp Ile Ala Met Met
                 85                  90                  95

His Leu Glu Met Lys Val Asn Tyr Thr Asp Tyr Ile Gln Pro Ile Cys
            100                 105                 110

Leu Pro Glu Glu Asn Gln Val Phe Pro Pro Gly Arg Ile Cys Ser Ile
        115                 120                 125

Ala Gly Trp Gly Ala Leu Ile Tyr Gln Gly Ser Thr Ala Asp Val Leu
    130                 135                 140

Gln Glu Ala Asp Val Pro Leu Leu Ser Asn Glu Lys Cys Gln Gln Gln
145                 150                 155                 160

Met Pro Glu Tyr Asn Ile Thr Glu Asn Met Val Cys Ala Gly Tyr Glu
                165                 170                 175

Ala Gly Gly Val Asp Ser Cys Gln Gly Asp Ser Gly Gly Pro Leu Met
            180                 185                 190

Cys Gln Glu Asn Asn Arg Trp Leu Leu Ala Gly Val Thr Ser Phe Gly
        195                 200                 205

Tyr Gln Cys Ala Leu Pro Asn Arg Pro Gly Val Tyr Ala Arg Val Pro
```

```
              210                 215                 220
Arg Phe Thr Glu Trp Ile Gln Ser Phe Leu His
225                 230                 235
```

<210> SEQ ID NO 4
<211> LENGTH: 710
<212> TYPE: DNA
<213> ORGANISM: Artificial Sequence
<220> FEATURE:
<223> OTHER INFORMATION: Polynucleotide molecule encoding an
      enterokinase light chain

<400> SEQUENCE: 4

```
atagttggcg gctctgactc cagagaaggt gcctggccat gggtcgttgc cttatacttt     60
gatgatcaac aggtctgtgg tgcttcactt gtttctagag attggttggt gtccgcagca    120
cattgtgtgt atggtaggaa tatggagcct tcaaagtgga agctgtatt ggggttgcat    180
atggcctcta accttacaag tccacaaatt gaaactagac taattgatca aattgttatc    240
aatcctcatt acaataagcg taggaaaaac aatgacatag caatgatgca cttggagatg    300
aaagttaact acacagacta catccaacca atatgtttgc ctgaggaaaa tcaggtgttc    360
ccacctggtc gtatttgtag tattgctgga tggggagccc tgatctacca aggatctacc    420
gctgacgtat tacaagaggc agatgttcct ctgctgtcca acgagaaatg ccagcaacaa    480
atgccagaat acaacatcac tgaaaacatg gtttgtgctg gttatgaagc tggaggtgta    540
gattcatgcc agggagattc aggcggtcct ctaatgtgcc aggagaataa ccgatggttg    600
cttgctggtg taacgagttt tggatatcaa tgcgctttac ctaaccgtcc aggggtctat    660
gcaagagtcc caagattcac cgagtggatt caatcttttc tgcactgagc                710
```

<210> SEQ ID NO 5
<211> LENGTH: 235
<212> TYPE: PRT
<213> ORGANISM: Artificial Sequence
<220> FEATURE:
<223> OTHER INFORMATION: Enterokinase light chain 1

<400> SEQUENCE: 5

```
Ile Val Gly Gly Ser Asp Ser Arg Glu Gly Ala Trp Pro Trp Val Val
1               5                   10                  15

Ala Leu Tyr Phe Asp Asp Gln Gln Val Cys Gly Ala Ser Leu Val Ser
                20                  25                  30

Arg Asp Trp Leu Val Ser Ala Ala His Cys Val Tyr Gly Arg Asn Met
            35                  40                  45

Glu Pro Ser Lys Trp Lys Ala Val Leu Gly Leu His Met Ala Ser Asn
        50                  55                  60

Leu Thr Ser Pro Gln Ile Glu Thr Arg Leu Ile Asp Gln Ile Val Ile
65                  70                  75                  80

Asn Pro His Tyr Asn Lys Arg Arg Lys Asn Asn Asp Ile Ala Met Met
                85                  90                  95

His Leu Glu Met Lys Val Asn Tyr Thr Asp Tyr Ile Gln Pro Ile Cys
                100                 105                 110

Leu Pro Glu Glu Asn Gln Val Phe Pro Pro Gly Arg Ile Cys Ser Ile
            115                 120                 125

Ala Gly Trp Gly Ala Leu Ile Tyr Gln Gly Ser Thr Ala Asp Val Leu
        130                 135                 140

Gln Glu Ala Asp Val Pro Leu Leu Ser Asn Glu Lys Cys Gln Gln Gln
145                 150                 155                 160
```

Met Pro Glu Tyr Asn Ile Thr Glu Asn Met Val Cys Ala Gly Tyr Glu
              165                 170                 175

Ala Gly Gly Val Asp Ser Cys Gln Gly Asp Ser Gly Pro Leu Met
            180                 185                 190

Cys Gln Glu Asn Asn Arg Trp Leu Leu Ala Gly Val Thr Ser Phe Gly
        195                 200                 205

Tyr Gln Cys Ala Leu Pro Asn Arg Pro Gly Val Tyr Ala Arg Val Pro
    210                 215                 220

Arg Phe Thr Glu Trp Ile Gln Ser Phe Leu His
225                 230                 235

<210> SEQ ID NO 6
<211> LENGTH: 953
<212> TYPE: DNA
<213> ORGANISM: Artificial Sequence
<220> FEATURE:
<223> OTHER INFORMATION: Polynucleotide molecule encoing the Alpha
      Factor and the enterokinase light chain

<400> SEQUENCE: 6
atgagatttc cttcaatttt tactgctgtt ttattcgcag catcctccgc attagctgct      60
ccagtcaaca ctacaacaga agatgaaacg gcacaaattc cggctgaagc tgtcatcggt    120
tactcagatt tagaagggga tttcgatgtt gctgttttgc cattttccaa cagcacaaat    180
aacgggttat tgtttataaa tactactatt gccagcattg ctgctaaaga agaaggggta    240
tctatagttg gcggctctga ctccagagaa ggtgcctggc catgggtcgt tgccttatac    300
tttgatgatc aacaggtctg tggtgcttca cttgtttcta gagattggtt ggtgtccgca    360
gcacattgtg tgtatggtag gaatatggag ccttcaaagt ggaaagctgt attgggggttg  420 catatggcct ctaaccttac aagtccacaa attgaaacta gactaattga tcaaattgtt    480
atcaatcctc attacaataa gcgtaggaaa acaatgaca tagcaatgat gcacttggag     540
atgaaagtta actacacaga ctacatccaa ccaatatgtt tgcctgagga aaatcaggtg    600
ttcccacctg tcgtatttg tagtattgct ggatggggag ccctgatcta ccaaggatct     660
accgctgacg tattacaaga ggcagatgtt cctctgctgt ccaacgagaa atgccagcaa    720
caaatgccag aatacaacat cactgaaaac atggtttgtg ctggttatga agctggaggt    780
gtagattcat gccagggaga ttcaggcggt cctctaatgt gccaggagaa taaccgatgg    840
ttgcttgctg gtgtaacgag ttttggatat caatgcgctt tacctaaccg tccaggggtc    900
tatgcaagag tcccaagatt caccgagtgg attcaatctt ttctgcactg agc           953

<210> SEQ ID NO 7
<211> LENGTH: 316
<212> TYPE: PRT
<213> ORGANISM: Artificial Sequence
<220> FEATURE:
<223> OTHER INFORMATION: Enterokinase with Alpha Factor signal sequence

<400> SEQUENCE: 7

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

```
Phe Ile Asn Thr Thr Ile Ala Ser Ile Ala Ala Lys Glu Glu Gly Val
 65                  70                  75                  80

Ser Ile Val Gly Gly Ser Asp Ser Arg Glu Gly Ala Trp Pro Trp Val
                 85                  90                  95

Val Ala Leu Tyr Phe Asp Asp Gln Gln Val Cys Gly Ala Ser Leu Val
            100                 105                 110

Ser Arg Asp Trp Leu Val Ser Ala Ala His Cys Val Tyr Gly Arg Asn
        115                 120                 125

Met Glu Pro Ser Lys Trp Lys Ala Val Leu Gly Leu His Met Ala Ser
    130                 135                 140

Asn Leu Thr Ser Pro Gln Ile Glu Thr Arg Leu Ile Asp Gln Ile Val
145                 150                 155                 160

Ile Asn Pro His Tyr Asn Lys Arg Arg Lys Asn Asn Asp Ile Ala Met
                165                 170                 175

Met His Leu Glu Met Lys Val Asn Tyr Thr Asp Tyr Ile Gln Pro Ile
            180                 185                 190

Cys Leu Pro Glu Glu Asn Gln Val Phe Pro Pro Gly Arg Ile Cys Ser
        195                 200                 205

Ile Ala Gly Trp Gly Ala Leu Ile Tyr Gln Gly Ser Thr Ala Asp Val
    210                 215                 220

Leu Gln Glu Ala Asp Val Pro Leu Leu Ser Asn Glu Lys Cys Gln Gln
225                 230                 235                 240

Gln Met Pro Glu Tyr Asn Ile Thr Glu Asn Met Val Cys Ala Gly Tyr
                245                 250                 255

Glu Ala Gly Gly Val Asp Ser Cys Gln Gly Asp Ser Gly Gly Pro Leu
            260                 265                 270

Met Cys Gln Glu Asn Asn Arg Trp Leu Leu Ala Gly Val Thr Ser Phe
        275                 280                 285

Gly Tyr Gln Cys Ala Leu Pro Asn Arg Pro Gly Val Tyr Ala Arg Val
    290                 295                 300

Pro Arg Phe Thr Glu Trp Ile Gln Ser Phe Leu His
305                 310                 315

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide primer for PCR

<400> SEQUENCE: 8
agatctaaca tccaaagacg aaagg                                        25

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide primer for PCR

<400> SEQUENCE: 9
gcagagcgag gtatgtaggc                                              20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide for PCR
```

```
<400> SEQUENCE: 10
cagatgttcc tctgctgtcc                                              20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer for PCR

<400> SEQUENCE: 11
atccactcgg tgaatcttgg                                              20
```

COMPOSITIONS AND METHODS OF PRODUCING ENTEROKINASE IN YEAST

This application claims priority pursuant to 35 U.S.C. §119 (e) to U.S. Provisional Patent Application No. 61/416,622, filed on Nov. 23, 2010, entirely incorporated by reference.

Enterokinase (EK, also known as Enteropeptidase (EP); EC 3.4.21.9) is a heterodimeric glycoprotein produced by cells of the duodenum. Part of the chymotrypsin-clan of serine proteases, it is secreted from intestinal glands (the crypts of Lieberkühn) following the entry of ingested food passing from the stomach and present in the duodenal and jejunal mucosa. Involved in the digestion of dietary proteins, EK catalyzes the cleavage of an N-terminal acidic peptide fragment from trypsinogen, converting this zymogen into its active form trypsin. The activation of trypsin initiates a cascade of proteolytic reactions leading to the activation of many pancreatic zymogens, including chymotrypsinogen, proelastase, procarboxypeptidases, and some prolipases.

Enterokinase has been cloned from several mammalian sources, including, e.g., humans, cattle, rats, and mice. Structurally, EK is a serine protease comprising an about 82-140 kDa heavy chain which anchors enterokinase in the intestinal brush border membrane and an about 35-62 kDa light chain which contains the catalytic subunit. The light chain is joined to the heavy chain via a single disulphide bridge. In addition to this single inter-domain disulphide bridge, the light chain contains a further eight cysteine residues which have been shown to form specific intra-domain disulphide bonds. The enterokinase light chain contains the catalytic activity and is sufficient for cleavage. EK and catalytically active fragments thereof are highly specific for the penta-peptide sequence Asp-Asp-Asp-Asp-Lys (SEQ ID NO: 1), cleaving the scissile bond located after the lysine residue (DDDDKθ).

Because of the high degree of specificity, EK has been used as a suitable reagent in biochemical and biotechnology applications. For example, a fusion protein containing a C-terminal purification tag (such as poly-His) linked by this sequence by EK cleavage site can be cleaved by EK to remove the purification tag in order to obtain the target protein following protein purification. Alternatively, the N-terminal pro-sequence of proteases which must be cleaved prior to activation can be mutated to enable activation with enterokinase.

Recombinant enterokinase (rEK) has been successfully produced in both the bacteria like *Escherichia coli* and yeast like *Pichia pastoris* utilizing a gene that produces a 28 kDa protein that encompasses only the catalytic light chain domain. However, difficulties still remain in terms of expressing this recombinant enzyme in yields sufficient enough for commercial applications. The present specification disclosed improved expression construction useful for producing recombinant enterokinase in a cost-effective manner and in amounts useful for commercial applications.

SUMMARY

Aspects of the present specification disclose polynucleotide molecules encoding enterokinase. The disclosed polynucleotide molecules encoding enterokinase include, without limitation, SEQ ID NO: 4, SEQ ID NO: 6, a nucleotide variant thereof, a truncated variant thereof, and/or a compliment thereof. A polynucleotide disclosed herein may further comprise a yeast expression vector. Other aspects disclose a yeast expression construct comprising a yeast expression vector and a polynucleotide molecule encoding enterokinase.

Other aspects of the present specification disclose yeast cells comprising a yeast expression construct including a polynucleotide molecule encoding enterokinase. The disclosed yeast expression constructs may be transiently contained in a yeast cell or it may be stably contained in the yeast cell. A yeast cell includes, without limitation, a cell from a *Pichia pastoris* strain, a cell from a *Pichia methanolica* strain, a cell from a *Pichia angusta* strain, a cell from a *Schizosaccharomyces pombe* strain, a cell from a *Saccharomyces cerevisiae* strain or a cell from a *Yarrowia lipolytica* strain.

Yet other aspects of the present specification disclose methods of producing an enterokinase using a yeast expression construct. The disclosed methods comprise the step of expressing in a yeast cell a yeast expression construct disclosed herein. Other aspect provide methods of producing an enterokinase comprising the steps of introducing a yeast expression construct disclosed herein into a yeast cell and expressing the expression construct in the yeast cell.

Still other aspects of the present specification disclose methods for cleaving a polypeptide comprising an enterokinase cleavage site using an enterokinase. The disclosed methods comprise the step of contacting the polypeptide including an enterokinase cleavage site with an enterokinase wherein contacting the polypeptide with the enterokinase results in a specific cleavage of the enterokinase cleavage site. The enterokinase used may be one encoded by a polynucleotide molecule disclosed herein, produced using a yeast expression construct disclosed herein, and/or produced by expressing in a yeast cell disclosed herein.

Other aspects of the present specification disclose methods for preparing a polypeptide comprising an enterokinase cleavage site using an enterokinase. The disclosed methods comprise the step of contacting the polypeptide including an enterokinase cleavage site with an enterokinase wherein contacting the polypeptide with the enterokinase results in a specific cleavage of the enterokinase cleavage site. The enterokinase used may be one encoded by a polynucleotide molecule disclosed herein, produced using a yeast expression construct disclosed herein, and/or produced by expressing in a yeast cell disclosed herein.

BRIEF DESCRIPTION OF THE DRAWINGS

FIG. 1 shows a graph of mean enzymatic activity of enterokinase produced from six different yeast cell lines comprising an integrated EK cassette disclosed herein.

DESCRIPTION

Yeast expression systems offer several advantages as a production system for a heterologous polypeptide. Firstly, yeast cells can be grown to high biomass (>300 g/L wet cell weight) in fermentors, providing dense cultures in order to produce large amounts of the desired polypeptide. Second, unlike prokaryotic expression systems, yeast expression systems can correctly govern post-translational folding and other modifications specific to an eukaryotic polypeptide, thereby ensuring the retention of biological activity, function and stability of the heterologous polypeptide. Third, yeast expression systems are versatile and flexible, offering 1) extrachromosomal or genome-based expression; 2) constitutive or inducible control of expression, and 3) the ability to direct the expressed heterologous polypeptide to specific cellular or extracellular compartments to facilitate isolation and purification.

The present specification discloses improved expression construction useful for producing recombinant enterokinase in a cost-effective manner and in amounts large enough to be useful for commercial applications. These results can be achieved using any one of the disclosed genetically-engineered polynucleotide molecules encoding enterokinase. Once cloned into a yeast expression vector and introduced into a yeast cell, these engineered molecules can produce significantly higher amounts of enterokinase then is currently possible.

Thus, aspects of the present specification provide, in part, a polynucleotide molecule. A polynucleotide molecule disclosed herein can be single-stranded or double-stranded DNA isolated from the genome of an organism, a recombinantly produced cDNA, of a chemically synthesized DNA molecule. Moreover, an "isolated" polynucleotide molecule is typically substantially free of other cellular materials when isolated from a genomic source or produced by recombinant techniques, or substantially free of chemical precursors or other chemicals when chemically synthesized.

Aspects of the present specification provide, in part, a polynucleotide molecule encoding enterokinase. As used herein, the term "enterokinase" is synonymous with "EK" and refers to any polypeptide that can selectively recognize and cleave the penta-peptide sequence Asp-Asp-Asp-Asp-Lys (SEQ ID NO: 1) at the scissile bond located after the lysine residue (DDDDK). As used herein, the term "selectively recognize and cleave" when made in reference to an enterokinase, refers to the discriminatory interaction of an enterokinase with a molecule comprising SEQ ID NO: 1 and the cleavage of the scissile bond located after the lysine residue of SEQ ID NO: 1, while not substantially interacting with and cleaving any other penta-peptide sequence located in the molecule. As such, enterokinase refers to the native heterodimeric glycoprotein comprising an about 82-140 kDa heavy chain and an about 35-62 kDa light chain joined by a single disulphide bridge as well as any catalytically active light chain fragment. Examples of making a polynucleotide molecule encoding enterokinase are described in Examples 1, 2, and 4-6.

In an embodiment, a polynucleotide molecule encoding enterokinase may be SEQ ID NO: 4, SEQ ID NO: 6, or a complement thereof. As used herein, the term "complement" refers to a polynucleotide molecule that is the anti-sense molecule to the sense molecule encoding the enterokinase. A polynucleotide molecule encoding enterokinase may include polynucleotide regions encoding other types of polypeptide molecules such as, e.g., purification tags, cell secretion signals, and/or subcellular localization signals. An exemplary polynucleotide molecule of such sort is SEQ ID NO: 6. A polynucleotide molecule encoding enterokinase may also include control or regulatory polynucleotide regions that direct or facilitate, e.g., aspects of transcription, translation, and/or post-translation processing.

In another embodiment, a polynucleotide molecule encoding enterokinase may be a nucleotide variant of SEQ ID NO: 4, SEQ ID NO: 6, or a complement thereof, with the proviso that the nucleotide change in SEQ ID NO: 4 or SEQ ID NO: 6, or a complement thereof does not alter the amino acid sequence of the enterokinase encoded by the polynucleotide variant. As such, a SEQ ID NO: 4 polynucleotide variant disclosed herein encodes the enterokinase of SEQ ID NO: 5, and a SEQ ID NO: 6 polynucleotide variant disclosed herein encodes the enterokinase of SEQ ID NO: 7.

In aspects of this embodiment, a polynucleotide variant molecule encoding enterokinase may be, e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical to the polynucleotide sequence of SEQ ID NO: 4, SEQ ID NO: 6, or a complement thereof.

In other aspects of this embodiment, a polynucleotide variant molecule encoding enterokinase may have from, e.g., about 1 to about 10, about 1 to about 15, about 1 to about 20, about 1 to about 25, about 1 to about 30, about 5 to about 25, about 5 to about 30, about 5 to about 35, about 5 to about 40, about 5 to about 45, about 10 to about 40, about 10 to about 45, about 10 to about 50, about 10 to about 55, or about 10 to about 60 non-contiguous nucleotide substitutions relative to SEQ ID NO: 4, SEQ ID NO: 6, or a complement thereof. In yet other aspects of this embodiment, a polynucleotide variant molecule encoding enterokinase may have, e.g., about 1 to about 10, about 1 to about 15, about 1 to about 20, about 1 to about 25, about 1 to about 30, about 5 to about 25, about 5 to about 30, about 5 to about 35, about 5 to about 40, about 5 to about 45, about 10 to about 40, about 10 to about 45, about 10 to about 50, about 10 to about 55, or about 10 to about 60 contiguous nucleotide substitutions relative to SEQ ID NO: 4, SEQ ID NO: 6, or a complement thereof.

Any of a variety of sequence alignment methods can be used to determine percent identity of a polynucleotide or polypeptide disclosed herein, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W: Improving the Sensitivity of Progressive Multiple Sequence Alignment Through Sequence Weighting, Position-Specific Gap Penalties and Weight Matrix Choice*, 22(22) Nucleic Acids Research 4673-4680 (1994); and iterative refinement, see, e.g., Osamu Gotoh, Significant Improvement in *Accuracy of Multiple Protein Sequence Alignments by Iterative Refinement as Assessed by Reference to Structural Alignments*, 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences*, 8(5) CABIOS 501-509 (1992); Gibbs sampling, see, e.g., C. E. Lawrence et al., *Detecting Subtle Sequence Signals: A Gibbs Sampling Strategy for Multiple Alignment*, 262(5131) Science 208-214 (1993); Align-M, see, e.g., Ivo Van Walle et al., *Align-M—A New Algorithm for Multiple Alignment of Highly Divergent Sequences*, 20(9) Bioinformatics:1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison*, 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment*, 302(1) J. Mol. Biol. 205-217 (2000); MUSCLE, see, e.g., Robert C. Edgar, *MUSCLE: Multiple Sequence Alignment With High Score Accuracy and High Throughput*, 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment*, 6(1) BMC Bioinformatics 66 (2005).

In yet aspects of this embodiment, a polynucleotide variant molecule encoding enterokinase may be polynucleotide variant that hybridizes to a polynucleotide molecule comprising SEQ ID NO: 4, SEQ ID NO: 6, or a complement thereof, under stringent conditions. Such stringent hybridization conditions are known to those skilled in the art and can be found in, e.g., Current Protocols in Molecular Biology, John Wiley & Sons, N.Y. (1989), 6.3.1-6.3.6, entirely incorporated by reference. A non-limiting example of stringent (e.g. high stringency) hybridization conditions are hybridization in 6× sodium chloride/sodium citrate (SSC) at about 45° C., followed by one or more washes in 0.2×SSC, 0.1% SDS at 50-65° C.

In still other aspects of this embodiment, a polynucleotide variant molecule encoding enterokinase may be a polynucleotide variant disclosed in Table 1. This table includes the amino acid sequence of enterokinase light chain, the codons comprising the open reading frame of the polynucleotide region of SEQ ID NO: 4 and SEQ ID NO: 6 encoding this light chain fragment, and the codon variants that can be substituted for the codons of SEQ ID NO: 4 and SEQ ID NO: 6. In aspects of this embodiment, a polynucleotide variant molecule encoding enterokinase has, e.g., 1, 2, 3, 4, 5, 6, 7, 8, 9, 10, 11, 12, 13, 14, 15, 16, 17, 18, 19, or 20 variant codons of Table 1 substituted for the corresponding codons presence in SEQ ID NO: 4 or SEQ ID NO: 6. In other aspects of this embodiment, a polynucleotide variant molecule encoding enterokinase has, e.g., at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, variant codons of Table 1 substituted for the corresponding codon presence in SEQ ID NO: 4 or SEQ ID NO: 6. In yet other aspects of this embodiment, a polynucleotide variant molecule encoding enterokinase has, e.g., at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, or at most 20 variant codons of Table 1 substituted for the corresponding codon presence in SEQ ID NO: 4 or SEQ ID NO: 6.

TABLE 1

Nucleic Acid Sequences of Enterokinase

| | | | | | | | | | | |
|---|---|---|---|---|---|---|---|---|---|---|
| Amino acid | I | V | G | G | S | D | S | R | E | G | A | W |
| Codon | ATA | GTT | GGC | GGC | TCT | GAC | TCC | AGA | GAA | GGT | GCC | TGG |
| Variant | ATT<br>ATC | — | GGT<br>GGA | GGT<br>GGA | — | GAT | TCT | — | — | GGA | GCT | — |

| | | | | | | | | | | |
|---|---|---|---|---|---|---|---|---|---|---|
| Amino acid | P | W | V | V | A | L | Y | F | D | D | Q | Q |
| Codon | CCA | TGG | GTC | GTT | GCC | TTA | TAC | TTT | GAT | GAT | CAA | CAG |
| Variant | CCT | — | GTT | — | GCT | TTG | TAT | — | — | — | — | CAA |

| | | | | | | | | | |
|---|---|---|---|---|---|---|---|---|---|
| Amino acid | V | C | G | A | S | L | V | S | R | D | W | L |
| Codon | GTC | TGT | GGT | GCT | TCA | CTT | GTT | TCT | AGA | GAT | TGG | TTG |
| Variant | GTT | — | GGA | — | TCT | TTG | — | — | — | — | — | — |

| | | | | | | | | | |
|---|---|---|---|---|---|---|---|---|---|
| Amino acid | V | S | A | A | H | C | V | Y | G | R | N | M |
| Codon | GTG | TCC | GCA | GCA | CAT | TGT | GTG | TAT | GGT | AGG | AAT | ATG |
| Variant | GTT | TCT | GCT | GCT | — | — | GTT | TAC | GGA | AGA | CAA | — |

| | | | | | | | | | |
|---|---|---|---|---|---|---|---|---|---|
| Amino acid | E | P | S | K | W | K | A | V | L | G | L | H |
| Codon | GAG | CCT | TCA | AAG | TGG | AAA | GCT | GTA | TTG | GGG | TTG | CAT |
| Variant | GAA | CCA | TCT | — | — | AAG | — | GTT | — | GGT | — | —<br>GGA |

| | | | | | | | | | |
|---|---|---|---|---|---|---|---|---|---|
| Amino acid | M | A | S | N | L | T | S | P | Q | I | E | T |
| Codon | ATG | GCC | TCT | AAC | CTT | ACA | AGT | CCA | CAA | ATT | GAA | ACT |
| Variant | — | GCT | — | — | TTG | ACT | TCT | CCT | — | ATC | — | — |

TABLE 1-continued

Nucleic Acid Sequences of Enterokinase

| | | | | | | | | | |
|---|---|---|---|---|---|---|---|---|---|
| Amino acid | R | L | I | D | Q | I | V | I | N | P | H | Y |
| Codon | AGA | CTA | ATT | GAT | CAA | ATT | GTT | ATC | AAT | CCT | CAT | TAC |
| Variant | — | TTG | ATC | — | — | ATC | — | ATT | AAC | CCA | — | — |

| | | | | | | | | | |
|---|---|---|---|---|---|---|---|---|---|
| Amino acid | N | K | R | R | K | N | N | D | I | A | M | M |
| Codon | AAT | AAG | CGT | AGG | AAA | AAC | AAT | GAC | ATA | GCA | ATG | ATG |
| Variant | AAC | — | AGA | AGA | AAG | — | AAC | GAT | ATT<br>ATC | GCT | — | — |

| | | | | | | | | | |
|---|---|---|---|---|---|---|---|---|---|
| Amino acid | H | L | E | M | K | V | N | Y | T | D | Y | I |
| Codon | CAC | TTG | GAG | ATG | AAA | GTT | AAC | TAC | ACA | GAC | TAC | ATC |
| Variant | CAT | — | GAA | — | AAG | — | — | — | ACT | GAT | — | ATT |

| | | | | | | | | |
|---|---|---|---|---|---|---|---|---|
| Amino acid | Q | P | I | C | L | P | E | E | N | Q | V | F |
| Codon | CAA | CCA | ATA | TGT | TTG | CCT | GAG | GAA | AAT | CAG | GTG | TTC |
| Variant | — | CCT | ATT<br>ATC | — | — | CCA | GAA | — | AAC | CAA | GTT | TTT |

| | | | | | | | | |
|---|---|---|---|---|---|---|---|---|
| Amino acid | P | P | G | R | I | C | S | I | A | G | W | G |
| Codon | CCA | CCT | GGT | CGT | ATT | TGT | AGT | ATT | GCT | GGA | TGG | GGA |
| Variant | CCT | CCA | GGA | AGA | ATC | — | TCT | ATC | — | GGT | — | GGT |

| | | | | | | | | | |
|---|---|---|---|---|---|---|---|---|---|
| Amino acid | A | L | I | Y | Q | G | S | T | A | D | V | L |
| Codon | GCC | CTG | ATC | TAC | CAA | GGA | TCT | ACC | GCT | GAC | GTA | TTA |
| Variant | GCT | TTG | ATT | — | — | GGT | — | ACT | — | GAT | GTT | TTG |

| | | | | | | | | | |
|---|---|---|---|---|---|---|---|---|---|
| Amino acid | Q | E | A | D | V | P | L | L | S | N | E | K |
| Codon | CAA | GAG | GCA | GAT | GTT | CCT | CTG | CTG | TCC | AAC | GAG | AAA |
| Variant | — | GAA | GCT | — | — | CCA | TTG | TTG | TCT | — | GAA | AAG |

| | | | | | | | | | |
|---|---|---|---|---|---|---|---|---|---|
| Amino acid | C | Q | Q | Q | M | P | E | Y | N | I | T | E |
| Codon | TGC | CAG | CAA | CAA | ATG | CCA | GAA | TAC | AAC | ATC | ACT | GAA |
| Variant | — | CAA | — | — | — | CCT | — | — | — | ATT | — | — |

| | | | | | | | | | |
|---|---|---|---|---|---|---|---|---|---|
| Amino acid | N | M | V | C | A | G | Y | E | A | G | G | V |
| Codon | AAC | ATG | GTT | TGT | GCT | GGT | TAT | GAA | GCT | GGA | GGT | GTA |
| Variant | — | — | — | — | — | GGA | TAC | — | — | GGT | GGA | GTT |

| | | | | | | | | | |
|---|---|---|---|---|---|---|---|---|---|
| Amino acid | D | S | C | Q | G | D | S | G | G | P | L | M |
| Codon | GAT | TCA | TGC | CAG | GGA | GAT | TCA | GGC | GGT | CCT | CTA | ATG |
| Variant | — | TCT | — | CAA | GGT | — | TCT | GGT | GGA | CCA | TTG | —<br>GGA |

| | | | | | | | | | |
|---|---|---|---|---|---|---|---|---|---|
| Amino acid | C | Q | E | N | N | R | W | L | L | A | G | V |
| Codon | TGC | CAG | GAG | AAT | AAC | CGA | TGG | TTG | CTT | GCT | GGT | GTA |
| Variant | — | CAA | GAA | AAC | — | AGA | — | — | TTG | — | GGA | GTT |

| | | | | | | | | | |
|---|---|---|---|---|---|---|---|---|---|
| Amino acid | T | S | F | G | Y | Q | C | A | L | P | N | R |
| Codon | ACG | AGT | TTT | GGA | TAT | CAA | TGC | GCT | TTA | CCT | AAC | CGT |
| Variant | ACT | TCT | — | GGT | TAC | — | — | — | TTG | CCA | — | AGA |

| | | | | | | | | | |
|---|---|---|---|---|---|---|---|---|---|
| Amino acid | P | G | V | Y | A | R | V | P | R | F | T | E |
| Codon | CCA | GGG | GTC | TAT | GCA | AGA | GTC | CCA | AGA | TTC | ACC | GAG |
| Variant | CCT | GGT | GTT | TAC | GCT | — | GTT | CCT | — | TTT | ACT | GAA<br>GGA |

| | | | | | |
|---|---|---|---|---|---|
| Amino acid | W | I | Q | S | F | L | H | * |
| Codon | TGG | ATT | CAA | TCT | TTT | CTG | CAC | TGA |
| Variant | — | ATC | — | — | — | TTG | CAT | TAA |

In further aspects of this embodiment, a polynucleotide molecule encoding enterokinase may be a polynucleotide variant disclosed in Table 2. This table includes the amino acid sequence of enterokinase light chain, the codons comprising the open reading frame of the polynucleotide region of SEQ ID NO: 4 and SEQ ID NO: 6 encoding this light chain fragment, and the codon variants that can be substituted for the codons of SEQ ID NO: 4 and SEQ ID NO: 6. In aspects of this embodiment, a polynucleotide variant molecule encoding enterokinase has, e.g., 1, 2, 3, 4, 5, 6, 7, 8, 9, 10, 11, 12, 13, 14, 15, 16, 17, 18, 19, or 20 variant codons of Table 2 substituted for the corresponding codon presence in SEQ ID NO: 4 or SEQ ID NO: 6. In other aspects of this embodiment, a polynucleotide variant molecule encoding enterokinase has, e.g., at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, variant codons of Table 2 substituted for the corresponding codon presence in SEQ ID NO: 4 or SEQ ID NO: 6. In other aspects of this embodiment, a polynucleotide variant molecule encoding enterokinase has, e.g., at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, or at most 20 variant codons of Table 2 substituted for the corresponding codon presence in SEQ ID NO: 4 or SEQ ID NO: 6.

TABLE 2

Nucleic Acid Sequences of Enterokinase

| Amino acid | I | V | G | G | S | D | S | R | E | G | A | W |
|---|---|---|---|---|---|---|---|---|---|---|---|---|
| Codon | ATA | GTT | GGC | GGC | TCT | GAC | TCC | AGA | GAA | GGT | GCC | TGG |
| Variant | ATT | — | GGT | GGT | — | GAT | TCT | — | — | — | GCT | — |

| Amino acid | P | W | V | V | A | L | Y | F | D | D | Q | Q |
|---|---|---|---|---|---|---|---|---|---|---|---|---|
| Codon | CCA | TGG | GTC | GTT | GCC | TTA | TAC | TTT | GAT | GAT | CAA | CAG |
| Variant | — | — | GTT | — | GCT | TTG | TAT | — | — | — | — | CAA |

| Amino acid | V | C | G | A | S | L | V | S | R | D | W | L |
|---|---|---|---|---|---|---|---|---|---|---|---|---|
| Codon | GTC | TGT | GGT | GCT | TCA | CTT | GTT | TCT | AGA | GAT | TGG | TTG |
| Variant | GTT | — | — | — | TCT | TTG | — | — | — | — | — | — |

| Amino acid | V | S | A | A | H | C | V | Y | G | R | N | M |
|---|---|---|---|---|---|---|---|---|---|---|---|---|
| Codon | GTG | TCC | GCA | GCA | CAT | TGT | GTG | TAT | GGT | AGG | AAT | ATG |
| Variant | GTT | TCT | GCT | GCT | — | — | GTT | TAC | — | AGA | CAA | — |

| Amino acid | E | P | S | K | W | K | A | V | L | G | L | H |
|---|---|---|---|---|---|---|---|---|---|---|---|---|
| Codon | GAG | CCT | TCA | AAG | TGG | AAA | GCT | GTA | TTG | GGG | TTG | CAT |
| Variant | GAA | CCA | TCT | — | — | AAG | — | GTT | — | GGT | — | — |

| Amino acid | M | A | S | N | L | T | S | P | Q | I | E | T |
|---|---|---|---|---|---|---|---|---|---|---|---|---|
| Codon | ATG | GCC | TCT | AAC | CTT | ACA | AGT | CCA | CAA | ATT | GAA | ACT |
| Variant | — | GCT | — | — | TTG | ACT | TCT | — | — | — | — | — |

| Amino acid | R | L | I | D | Q | I | V | I | N | P | H | Y |
|---|---|---|---|---|---|---|---|---|---|---|---|---|
| Codon | AGA | CTA | ATT | GAT | CAA | ATT | GTT | ATC | AAT | CCT | CAT | TAC |
| Variant | — | TTG | — | — | — | — | — | ATT | AAC | CCA | — | — |

| Amino acid | N | K | R | R | K | N | N | D | I | A | M | M |
|---|---|---|---|---|---|---|---|---|---|---|---|---|
| Codon | AAT | AAG | CGT | AGG | AAA | AAC | AAT | GAC | ATA | GCA | ATG | ATG |
| Variant | AAC | — | AGA | AGA | AAG | — | AAC | GAT | ATT | GCT | — | — |

| Amino acid | H | L | E | M | K | V | N | Y | T | D | Y | I |
|---|---|---|---|---|---|---|---|---|---|---|---|---|
| Codon | CAC | TTG | GAG | ATG | AAA | GTT | AAC | TAC | ACA | GAC | TAC | ATC |
| Variant | CAT | — | GAA | — | AAG | — | — | — | ACT | GAT | — | ATT |

| Amino acid | Q | P | I | C | L | P | E | E | N | Q | V | F |
|---|---|---|---|---|---|---|---|---|---|---|---|---|
| Codon | CAA | CCA | ATA | TGT | TTG | CCT | GAG | GAA | AAT | CAG | GTG | TTC |
| Variant | — | — | ATT | — | — | CCA | GAA | — | AAC | CAA | GTT | TTT |

| Amino acid | P | P | G | R | I | C | S | I | A | G | W | G |
|---|---|---|---|---|---|---|---|---|---|---|---|---|
| Codon | CCA | CCT | GGT | CGT | ATT | TGT | AGT | ATT | GCT | GGA | TGG | GGA |
| Variant | — | CCA | — | AGA | — | — | TCT | — | — | GGT | — | GGT |

| Amino acid | A | L | I | Y | Q | G | S | T | A | D | V | L |
|---|---|---|---|---|---|---|---|---|---|---|---|---|
| Codon | GCC | CTG | ATC | TAC | CAA | GGA | TCT | ACC | GCT | GAC | GTA | TTA |
| Variant | GCT | TTG | ATT | — | — | GGT | — | ACT | — | GAT | GTT | TTG |

| Amino acid | Q | E | A | D | V | P | L | L | S | N | E | K |
|---|---|---|---|---|---|---|---|---|---|---|---|---|
| Codon | CAA | GAG | GCA | GAT | GTT | CCT | CTG | CTG | TCC | AAC | GAG | AAA |
| Variant | — | GAA | GCT | — | — | CCA | TTG | TTG | TCT | — | GAA | AAG |

| Amino acid | C | Q | Q | Q | M | P | E | Y | N | I | T | E |
|---|---|---|---|---|---|---|---|---|---|---|---|---|
| Codon | TGC | CAG | CAA | CAA | ATG | CCA | GAA | TAC | AAC | ATC | ACT | GAA |
| Variant | — | CAA | — | — | — | — | — | — | — | ATT | — | — |

TABLE 2-continued

Nucleic Acid Sequences of Enterokinase

| Amino acid | N | M | V | C | A | G | Y | E | A | G | G | V |
|---|---|---|---|---|---|---|---|---|---|---|---|---|
| Codon | AAC | ATG | GTT | TGT | GCT | GGT | TAT | GAA | GCT | GGA | GGT | GTA |
| Variant | — | — | — | — | — | — | TAC | — | — | GGT | — | GTT |

| Amino acid | D | S | C | Q | G | D | S | G | G | P | L | M |
|---|---|---|---|---|---|---|---|---|---|---|---|---|
| Codon | GAT | TCA | TGC | CAG | GGA | GAT | TCA | GGC | GGT | CCT | CTA | ATG |
| Variant | — | TCT | — | CAA | GGT | — | TCT | GGT | — | CCA | TTG | — |

| Amino acid | C | Q | E | N | N | R | W | L | L | A | G | V |
|---|---|---|---|---|---|---|---|---|---|---|---|---|
| Codon | TGC | CAG | GAG | AAT | AAC | CGA | TGG | TTG | CTT | GCT | GGT | GTA |
| Variant | — | CAA | GAA | AAC | — | AGA | — | — | TTG | — | — | GTT |

| Amino acid | T | S | F | G | Y | Q | C | A | L | P | N | R |
|---|---|---|---|---|---|---|---|---|---|---|---|---|
| Codon | ACG | AGT | TTT | GGA | TAT | CAA | TGC | GCT | TTA | CCT | AAC | CGT |
| Variant | ACT | TCT | — | GGT | TAC | — | — | — | TTG | CCA | — | AGA |

| Amino acid | P | G | V | Y | A | R | V | P | R | F | T | E |
|---|---|---|---|---|---|---|---|---|---|---|---|---|
| Codon | CCA | GGG | GTC | TAT | GCA | AGA | GTC | CCA | AGA | TTC | ACC | GAG |
| Variant | — | GGT | GTT | TAC | GCT | — | GTT | — | — | TTT | ACT | GAA |

| Amino acid | W | I | Q | S | F | L | H | * |
|---|---|---|---|---|---|---|---|---|
| Codon | TGG | ATT | CAA | TCT | TTT | CTG | CAC | TGA |
| Variant | — | — | — | — | — | TTG | CAT | TAA |

In yet another embodiment, the polynucleotide molecule encoding enterokinase may be a truncated fragment of SEQ ID NO: 4, SEQ ID NO: 6, or a nucleotide variant thereof. As used herein, the term "truncated fragment of SEQ ID NO: 4, SEQ ID NO: 6, or any nucleotide variant thereof" refers to the removal of nucleotides from the 710 nucleotide sequence embodied by SEQ ID NO: 4 or a nucleotide variant thereof, or the 953 nucleotide sequence embodied by SEQ ID NO: 6 or a nucleotide variant thereof. Nucleotides from the 5'-end, the 3'-end, or both the 5'-end and 3'-end of SEQ ID NO: 4, SEQ ID NO: 6, or any nucleotide variant thereof may be removed.

In aspects of this embodiment, 1, 2, 3, 4, 5, 6, 7, 8, 9, 10, 11, 12, 13, 14, 15, 16, 17, 18, 19, 20, 25, 30, 35, 40, 45, or 50 nucleotides are removed from the 5'-end, the 3'-end, or both the 5'-end and 3'-end of SEQ ID NO: 4, SEQ ID NO: 6, or any nucleotide variant thereof, or compliment thereof. In other aspects of this embodiment, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50 nucleotides are removed from the 5'-end, the 3'-end, or both the 5'-end and 3'-end of SEQ ID NO: 4, SEQ ID NO: 6, or any nucleotide variant thereof, or compliment thereof. In yet other aspects of this embodiment, at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, at most 20, at most 25, at most 30, at most 35, at most 40, at most 45, or at most 50 nucleotides are removed from the 5'-end, the 3'-end, or both the 5'-end and 3'-end of SEQ ID NO: 4, SEQ ID NO: 6, or any nucleotide variant thereof, or compliment thereof.

In other aspects of this embodiment, 1, 2, 3, 4, 5, 6, 7, 8, 9, 10, 11, 12, 13, 14, 15, 16, 17, 18, 19, or 20 codons are removed from the 5'-end, the 3'-end, or both the 5'-end and 3'-end of SEQ ID NO: 4, SEQ ID NO: 6, or any nucleotide variant thereof, or compliment thereof. In other aspects of this embodiment, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, codons are removed from the 5'-end, the 3'-end, or both the 5'-end and 3'-end of SEQ ID NO: 4, SEQ ID NO: 6, or any nucleotide variant thereof, or compliment thereof. In yet other aspects of this embodiment, at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, or at most 20 codons are removed from the 5'-end, the 3'-end, or both the 5'-end and 3'-end of SEQ ID NO: 4, SEQ ID NO: 6, or any nucleotide variant thereof, or compliment thereof.

Aspects of the present specification disclose, in part, a polynucleotide molecule comprising a yeast expression vector. A wide variety of yeast expression vectors can be employed for expressing a polynucleotide molecule encoding EK, including, without limitation, a *Pichia pastoris* expression vector, a *Pichia methanolica* expression vector, a *Pichia angusta* expression vector, a *Schizosaccharomyces pombe* expression vector, a *Saccharomyces cerevisiae* expression vector and a *Yarrowia lipolytica* expression vector. Non-limiting examples of yeast expression vectors include a pGal-MF expression vector (DualsystemsBiotech, AG, Schlieren, CH), a pMET expression vector (Invitrogen, Inc., Carlsbad, Calif.), a PICHIAPINK expression vector (Invitrogen, Inc., Carlsbad, Calif.), a pPICZ expression vector (Invitrogen, Inc., Carlsbad, Calif.), a pPpT4Alpha expression vector (Ingenza, Ltd., Midlothian, UK), a pTEF-MF expression vector (DualsystemsBiotech, AG, Schlieren, CH), a pYES expression vector (Invitrogen, Inc., Carlsbad, Calif.).

A yeast expression vector typically include control or regulatory polynucleotide regions that direct or facilitate, e.g., aspects of replication, integration, transcription, translation, and/or post-translation processing. For example, a yeast expression vector can include constitutive promoter and enhancer elements and/or inducible promoter and enhancer elements used to direct EK expression. A non-limiting example of a constitutive expression vector is one that employs a Glyceraldehyde-3-Phosphate Dehydrogenase (GAP) promoter to direct EK production. A non-limiting example of an inducible expression vector is one that uses an Aldehyde Oxidase 1 (AOX1) promoter, with methanol as the inducer. In either case, high levels of expression can be achieved, with up to several grams per litre of product obtained. For example, in methanol induced yeast cells, AOX1 can account for 30% of the total soluble protein. Strains lacking the AOX1 gene (also called Mut$^S$ strains) can still be induced by methanol, since they express the alcohol oxidase 2 gene (AOX2), but they grow slower than wild type strains when methanol is used as the sole carbon source. However, instead of using energy and resources predominantly for AOX1 protein production, in Mut$^S$ strains the force of the AOX1 promoter can be directed mainly towards recombinant protein production. In addition lower methanol levels can be applied.

A yeast expression vector may include polynucleotide regions encoding other types of polypeptide molecules such as, e.g., purification tags, cell secretion signals, and/or subcellular localization signals. Such polynucleotide regions are usually operably-linked to the EK in the form of a fusion polypeptide. Non-limiting examples of purification tags include a histidine tag, a myc tag, a V5 tag. Non-limiting examples of signal sequences include those that direct the EK to the cell cytoplasm, a cellular organelle, such as a peroxisome, or to the extracellular culture medium. For instance, inclusion of the Alpha Factor peptide signal enables secretion of the EK into the culture medium.

Aspects of the present specification disclose, in part, a polynucleotide molecule comprising a yeast expression construct. A yeast expression construct comprises a polynucleotide molecule encoding EK as disclosed herein operably-linked to a yeast expression vector as disclosed herein. Examples of a yeast expression construct are described in Examples 2 and 4-6.

Aspects of the present specification disclose, in part, introducing into a yeast cell a polynucleotide molecule disclosed herein. A polynucleotide molecule introduced into a cell can be transiently or stably maintained by that cell. Stably-maintained polynucleotide molecules may be extra-chromosomal and replicate autonomously, or they may be integrated into the chromosomal material of the cell and replicate non-autonomously.

It is envisioned that any and all methods for introducing a polynucleotide molecule disclosed herein into a cell can be used. Methods useful for introducing a nucleic acid molecule into a cell include, without limitation, chemical-mediated transfection such as, e.g., calcium phosphate-mediated, diethyl-aminoethyl (DEAE) dextran-mediated, lipid-mediated, polyethyleneimine (PEI)-mediated, polylysine-mediated and polybrene-mediated; physical-mediated tranfection, such as, e.g., biolistic particle delivery, microinjection, protoplast fusion and electroporation; and viral-mediated transfection, such as, e.g., retroviral-mediated transfection. One skilled in the art understands that selection of a specific method to introduce an expression construct into a cell will depend, in part, on whether the cell will transiently contain an expression construct or whether the cell will stably contain an expression construct. These protocols are routine procedures within the scope of one skilled in the art and from the teaching herein, see, e.g., Introducing Cloned Genes into Cultured Mammalian Cells, pp. 16.1-16.62 (Sambrook & Russell, eds., Molecular Cloning A Laboratory Manual, Vol. 3, 3$^{rd}$ ed. 2001). Examples of introducing a yeast expression construct disclosed herein into a yeast cell are described in Examples 2 and 4-6.

Aspects of the present specification disclose, in part, a yeast cell comprising a yeast expression construct including a polynucleotide molecule encoding EK as disclosed herein. In an aspect of this embodiment, a yeast cell transiently contains a yeast expression construct including a polynucleotide molecule encoding EK as disclosed herein. In another aspect of this embodiment, a yeast cell stably contains an expression construct including a polynucleotide molecule encoding EK as disclosed herein. In aspects of this embodiment, a yeast cell is a yeast cell strain derived from *Pichia pastoris, Pichia methanolica, Pichia angusta, Schizosaccharomyces pombe, Saccharomyces cerevisiae* or *Yarrowia lipolytica*. In other aspects of this embodiment, a yeast expression construct is a *Pichia pastoris* expression vector, a *Pichia methanolica* expression vector, a *Pichia angusta* expression vector, a *Schizosaccharomyces pombe* expression vector, a *Saccharomyces cerevisiae* expression vector or a *Yarrowia lipolytica* expression vector. In yet other aspects of this embodiment, polynucleotide molecule encoding EK is SEQ ID NO: 4, SEQ ID NO: 6, or any nucleotide variant thereof, or a complement thereof.

Aspects of the present specification disclose, in part, expressing an EK from a polynucleotide molecule disclosed herein using a yeast expression system. Expression of a polynucleotide molecule using a yeast expression system can include any of a variety of characteristics including, without limitation, inducible expression, non-inducible expression, constitutive expression, viral-mediated expression, stably-integrated expression, and transient expression. These protocols are routine procedures well within the scope of one skilled in the art and from the teaching herein. Non-limiting examples of yeast expression systems include a EASYSE-LECT™ *Pichia* Expression Kit (Invitrogen, Inc., Carlsbad, Calif.), a EASYSELECT™ ECHO™ *Pichia* Expression Kit (Invitrogen, Inc., Carlsbad, Calif.), a *Pichia methanolica* Expression System (Invitrogen, Inc., Carlsbad, Calif.), a PICHIAPINK™ Secreted Protein Kit (Invitrogen, Inc., Carlsbad, Calif.), a YES-ECHO™ Expression Vector Kit (Invitrogen, Inc., Carlsbad, Calif.) and a SPECTRA™ *S. pombe* Expression System (Invitrogen, Inc., Carlsbad, Calif.). Examples of expressing an EK from a polynucleotide molecule disclosed herein using a yeast expression system are described in Examples 2-6.

In an embodiment, the amount of EK expressed from a yeast expression construct comprising a polynucleotide molecule of SEQ ID NO: 4, SEQ ID NO: 6, or any polynucleotide variant thereof is increased as compared to the amount of EK expressed from SEQ ID NO: 2.

In aspects of this embodiment, the amount of EK expressed from a yeast expression construct comprising a polynucleotide molecule of SEQ ID NO: 4, SEQ ID NO: 6, or any polynucleotide variant thereof is increased by, e.g., at least 0.5-fold, at least 1-fold, at least 1.5-fold, at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 30-fold, at least 35-fold, or at least 40-fold, as compared to the amount of EK expressed from SEQ ID NO: 2. In other aspects of this embodiment, the amount of EK expressed from a yeast expression construct comprising a polynucleotide molecule of SEQ ID NO: 4, SEQ ID NO: 6, or any polynucleotide variant thereof is increased by, e.g., about 1-fold to about 5-fold, about 1-fold to about 10-fold, about 1-fold to about 15-fold, about 1-fold to about 20-fold, about 1-fold to about 25-fold, as compared to the amount of EK expressed from SEQ ID NO: 2.

In other aspects of this embodiment, the amount of EK expressed from a yeast expression construct comprising a polynucleotide molecule of SEQ ID NO: 4, SEQ ID NO: 6, or any polynucleotide variant thereof is about 100 mg/L to about 30 g/L. In aspects of this embodiment, the amount of EK expressed from a polynucleotide molecule of SEQ ID NO: 4, SEQ ID NO: 6, or any polynucleotide variant thereof may be, e.g., at least 100 mg/L, at least 500 mg/L, at least 1 g/L, at least 1.5 g/L, at least 2.5 g/L, at least 5 g/L, at least 7.5 g/L, at least 10 g/L, at least 12.5 g/L, at least 15 g/L, at least 20 g/L, at least 25 g/L, or at least 30 g/L. In yet other aspects of this embodiment, the amount of EK expressed from a yeast expression construct comprising a polynucleotide molecule of SEQ ID NO: 4, SEQ ID NO: 6, or any polynucleotide variant thereof may be from, e.g., about 100 mg/L to about 5 g/L, about 100 mg/L to about 10 g/L, about 100 mg/L to about 15 g/L, about 500 mg/L to about 5 g/L, about 500 mg/L to about 10 g/L, about 500 mg/L to about 15 g/L, about 1 g/L to about 5 g/L, about 1 g/L to about 10 g/L, about 1 g/L to about 15 g/L, about 1 g/L to about 20 g/L, about 5 g/L to about 10 g/L, about 5 g/L to about 15 g/L, about 5 g/L to about 20 g/L, about 5 g/L to about 25 g/L, about 5 g/L to about 30 g/L.

An EK expressed from a yeast expression construct disclosed herein may be purified from the yeast cell or culture medium using any of a variety of methods. Examples of purification methods include, without limitation, ammonium sulfate or ethanol precipitation, acid extraction, ion exchange chromatography, phosphocellulose chromatography, lectin chromatography, affinity chromatography, hydrophobic interaction chromatography, size exclusion chromatography, gel-filtration chromatography, adsorption chromatography, hydroxyapatite chromatography, fast performance liquid chromatography (FPLC), and high performance liquid (HPLC) chromatography. Binding moieties of the target peptide of interest may be attached to any of a variety of substances including, without limitation resins, agarose, and magnetic beads. In addition, any of a variety of processing techniques can be used including, without limitation, batch-wise processing, and gravity-feed columns. Protein refolding steps may also be necessary to ensure recovery of a functionally active BoNT/A encoded by nucleic acid molecules disclosed in the specification. Non-limiting examples of specific protocols for purifying and recovering proteins are described in, e.g., John Abelson et al., Guide to Protein Purification, (Academic Press, 1990), Protein Purification: Principles and Practice, (Robert K. Scopes et al. eds., Springer Verlag, 3rd ed. 1994), Protein Purification Techniques: A Practical Approach, (Simon Roe ed., Oxford University Press, 2nd ed. 2001), Molecular Cloning A Laboratory Manual, supra, (2001), Ian M. Rosenberg, Protein Analysis & Purification: Benchtop Techniques, (Springer Verlag, 2002). These protocols are routine procedures within the scope of one skilled in the art and from the teaching herein.

EK amounts can be measured during EK expression, after completion of EK expression, and/or after EK purification using any of a variety of methods. Examples of protein measurement methods include, without limitation, gel electrophoresis and protein staining, Western blotting, ELISA, protein-labeling, UV absorbance, the Lowry assay, the biuret assay, the Smith copper/bicinchoninic (BCA) assay, and the Bradford dye assay, see e.g., Christine V. Sapan et al., *Colorimetric Protein Assay Techniques,* 29(2) Biotechnol. Appl. Biochem. 99-108, (1999).

Aspects of the present specification disclose, in part, methods for cleaving a polypeptide comprising an EK cleavage site using an EK. In one embodiment, a method for cleaving a polypeptide comprising an EK cleavage site includes the step of contacting the polypeptide including a EK cleavage site with an EK, the EK produced by expressing a yeast expression construct comprising SEQ ID NO: 4, SEQ ID NO: 6, any polynucleotide variant thereof, or any truncated variant thereof in a yeast cell, wherein contacting the recombinant polypeptide with the enterokinase results in a specific cleavage of the EK cleavage site. In an aspect of this embodiment, the EK cleavage site is SEQ ID NO: 1. The polypeptide may be one that naturally has an EK cleavage site or it may be a recombinant polypeptide that is genetically engineered to contain an EK cleavage site.

Aspects of the present specification disclose, in part, methods for preparing a polypeptide comprising an EK cleavage site using an EK. In one embodiment, a method for preparing of a polypeptide comprising an EK cleavage site includes the step of contacting the polypeptide including a EK cleavage site with an EK, the EK produced by expressing a yeast expression construct comprising SEQ ID NO: 4, SEQ ID NO: 6, any polynucleotide variant thereof, or any truncated variant thereof in a yeast cell, wherein contacting the recombinant polypeptide with the enterokinase results in a specific cleavage of the EK cleavage site. In an aspect of this embodiment, the EK cleavage site is SEQ ID NO: 1. The polypeptide may be one that maturally has an EK cleavage site or it may be a recombinant polypeptide that is genetically engineered to contain an EK cleavage site.

Methods of using EK to cleave or prepare a polypeptide comprising an EK cleavage site can be performed using a standard in vitro proteolytic cleavage assay. For example, a polypeptide comprising an EK cleavage site may be added to a reaction mixture comprising 20 mM Tris-HCl (pH 7.4), 50 mM NaCl, 20 mM $CaCl_2$ and an EK produced as described herein and incubated at about 20 to about 22° C. for about 2 hours to about 16 hours. The extent of cleaved or prepared polypeptide thus produced can be assessed using standard procedures, such as, e.g., SDS-PAGE analysis, an immuno-based assay like Western blot analysis or ELISA, or an activity assay for the polypeptide. The cleaved or prepared polypeptide may also be purified using standard procedures. Assays useful for cleaving or preparing a polypeptide comprising an EK cleavage site are described in, e.g., Ogiwara, et al., Modified Enteropeptidase Protein, U.S. Pat. No. 8,013, 137; La Vallie, Cloning of Enterokinase and Method of Use, U.S. Pat. No. 6,746,859, each entirely incorporated by reference.

Aspects of the present specification may also be described as follows:

1. An isolated polynucleotide molecule comprising SEQ ID NO: 4, SEQ ID NO: 6, a polynucleotide variant thereof, or a truncated variant thereof and any compliment thereof.
2. The isolated polynucleotide molecule of embodiment 1, wherein the polynucleotide variant is at least 70%, at least 75%, at least 80%, at least 85%, at least 90%, at least 91%, at least 92%, at least 93%, at least 94%, at least 95%, at least 96%, at least 97% at least 98%, or at least 99% identical to the polynucleotide sequence of SEQ ID NO: 4, SEQ ID NO: 6, or a complement thereof.
3. The isolated polynucleotide molecule of embodiment 1, wherein the polynucleotide variant has from about 1 to about 10, about 1 to about 15, about 1 to about 20, about 1 to about 25, about 1 to about 30, about 5 to about 25, about 5 to about 30, about 5 to about 35, about 5 to about 40, about 5 to about 45, about 10 to about 40, about 10 to about 45, about 10 to about 50, about 10 to about 55, or about 10 to about 60 non-contiguous nucleotide substitutions relative to SEQ ID NO: 4, SEQ ID NO: 6, or a complement thereof.
4. The isolated polynucleotide molecule of embodiment 1, wherein the polynucleotide variant has from about 1 to about 10, about 1 to about 15, about 1 to about 20, about 1 to about 25, about 1 to about 30, about 5 to about 25, about 5 to about 30, about 5 to about 35, about 5 to about 40, about 5 to about 45, about 10 to about 40, about 10 to about 45, about 10 to about 50, about 10 to about 55, or about 10 to about 60 contiguous nucleotide substitutions relative to SEQ ID NO: 4, SEQ ID NO: 6, or a complement thereof.
5. The isolated polynucleotide molecule of embodiment 1, wherein the polynucleotide variant hybridizes to a polynucleotide molecule comprising SEQ ID NO: 4, SEQ ID NO: 6, or a complement thereof, under stringent condition
6. The isolated polynucleotide molecule of embodiment 1, wherein the polynucleotide variant has at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, variant codons from Table 1 substituted for the corresponding codon presence in SEQ ID NO: 4 or SEQ ID NO: 6.
7. The isolated polynucleotide molecule of embodiment 1, wherein the polynucleotide variant has at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, variant codons from Table 2 substituted for the corresponding codon presence in SEQ ID NO: 4 or SEQ ID NO: 6.
8. The isolated polynucleotide molecule of embodiment 1, wherein the truncated variant has at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50 nucleotides removed from the 5'-end, the 3'-end, or both the 5'-end and 3'-end of SEQ ID NO: 4, SEQ ID NO: 6, or any nucleotide variant thereof, or any compliment thereof.
9. The isolated polynucleotide molecule of embodiment 1, wherein the truncated variant has at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, codons removed from the 5'-end, the 3'-end, or both the 5'-end and 3'-end of SEQ ID NO: 4, SEQ ID NO: 6, or any nucleotide variant thereof, or compliment thereof.
10. The isolated polynucleotide molecule of embodiments 1-9, wherein the isolated polynucleotide molecule is a yeast expression vector.
11. The isolated polynucleotide molecule of embodiment 10, wherein the yeast expression vector is a *Pichia pastoris* expression vector, a *Pichia methanolica* expression vector, a *Pichia angusta* expression vector, a *Schizosaccharomyces pombe* expression vector, a *Saccharomyces cerevisiae* expression vector and a *Yarrowia lipolytica* expression vector.
12. The isolated polynucleotide molecule of embodiment 10 or 11, wherein the yeast expression vector includes a constitutive promoter, a constitutive enhancer, an inducible promoter, an inducible enhancer, or any combination thereof that directs the expression of the polynucleotide molecule of embodiments 1-9.
13. The isolated polynucleotide molecule of embodiment 12, wherein the inducible promoter is an Aldehyde Oxidase 1 (AOX1) promoter.
14. The isolated polynucleotide molecule of embodiments 10-14, wherein the yeast expression vector includes a polynucleotide region encoding a signal sequence that directs the EK encoded by the polynucleotide molecule of embodiments 1-9 to a specific cellular or extracellular compartment.
15. The isolated polynucleotide molecule of embodiments 10-14, wherein the yeast expression vector includes a polynucleotide region encoding a signal sequence that directs the EK encoded by the polynucleotide molecule of embodiments 1-9 to the cell cytoplasm, a cellular organelle, or to the extracellular culture medium.
16. The isolated polynucleotide molecule of embodiment 14 or 15, wherein the signal sequence is an Alpha Factor peptide.
17. The isolated polynucleotide molecule of embodiments 1-9, wherein the isolated polynucleotide molecule is a yeast expression construct.
18. A yeast expression construct comprising a yeast expression vector and a polynucleotide molecule comprising SEQ ID NO: 4, SEQ ID NO: 6, a polynucleotide variant thereof, or a truncated variant thereof and any compliment thereof.
19. The yeast expression construct of embodiment 18, wherein the polynucleotide variant is at least 70%, at least 75%, at least 80%, at least 85%, at least 90%, at least 91%, at least 92%, at least 93%, at least 94%, at least 95%, at least 96%, at least 97% at least 98%, or at least 99% identical to the polynucleotide sequence of SEQ ID NO: 4, SEQ ID NO: 6, or a complement thereof.
20. The yeast expression construct of embodiment 18, wherein the polynucleotide variant has from about 1 to about 10, about 1 to about 15, about 1 to about 20, about 1 to about 25, about 1 to about 30, about 5 to about 25, about 5 to about 30, about 5 to about 35, about 5 to about 40, about 5 to about 45, about 10 to about 40, about 10 to about 45, about 10 to about 50, about 10 to about 55, or about 10 to about 60 non-contiguous nucleotide substitutions relative to SEQ ID NO: 4, SEQ ID NO: 6, or a complement thereof.

21. The yeast expression construct of embodiment 18, wherein the polynucleotide variant has from about 1 to about 10, about 1 to about 15, about 1 to about 20, about 1 to about 25, about 1 to about 30, about 5 to about 25, about 5 to about 30, about 5 to about 35, about 5 to about 40, about 5 to about 45, about 10 to about 40, about 10 to about 45, about 10 to about 50, about 10 to about 55, or about 10 to about 60 contiguous nucleotide substitutions relative to SEQ ID NO: 4, SEQ ID NO: 6, or a complement thereof.

22. The yeast expression construct of embodiment 18, wherein the polynucleotide variant hybridizes to a polynucleotide molecule comprising SEQ ID NO: 4, SEQ ID NO: 6, or a complement thereof, under stringent condition 23. The yeast expression construct of embodiment 18, wherein the polynucleotide variant has at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, variant codons from Table 1 substituted for the corresponding codon presence in SEQ ID NO: 4 or SEQ ID NO: 6.

24. The yeast expression construct of embodiment 18, wherein the polynucleotide variant has at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, variant codons from Table 2 substituted for the corresponding codon presence in SEQ ID NO: 4 or SEQ ID NO: 6.

25. The yeast expression construct of embodiment 18, wherein the truncated variant has at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50 nucleotides removed from the 5'-end, the 3'-end, or both the 5'-end and 3'-end of SEQ ID NO: 4, SEQ ID NO: 6, or any nucleotide variant thereof, or any compliment thereof.

26. The yeast expression construct of embodiment 18, wherein the truncated variant has at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, codons removed from the 5'-end, the 3'-end, or both the 5'-end and 3'-end of SEQ ID NO: 4, SEQ ID NO: 6, or any nucleotide variant thereof, or compliment thereof.

27. The yeast expression construct of embodiments 18-26, wherein the yeast expression vector is a *Pichia pastoris* expression vector, a *Pichia methanolica* expression vector, a *Pichia angusta* expression vector, a *Schizosaccharomyces pombe* expression vector, a *Saccharomyces cerevisiae* expression vector and a *Yarrowia lipolytica* expression vector.

28. The yeast expression construct of embodiment 27, wherein the yeast expression vector includes a constitutive promoter, a constitutive enhancer, an inducible promoter, an inducible enhancer, or any combination thereof that directs the expression of the polynucleotide molecule of embodiments 1-9.

29. The yeast expression construct of embodiment 28, wherein the inducible promoter is an Aldehyde Oxidase 1 (AOX1) promoter.

30. The yeast expression construct of embodiments 27-29, wherein the yeast expression vector includes a polynucleotide region encoding a signal sequence that directs the EK encoded by the polynucleotide molecule of embodiments 1-9 to a specific cellular or extracellular compartment.

31. The yeast expression construct of embodiments 27-29, wherein the yeast expression vector includes a polynucleotide region encoding a signal sequence that directs the EK encoded by the polynucleotide molecule of embodiments 1-9 to the cell cytoplasm, a cellular organelle, or to the extracellular culture medium.

32. The yeast expression construct of embodiment 30 or 31, wherein the signal sequence is an Alpha Factor peptide.

33. A yeast cell comprising a polynucleotide of embodiments 1-17.

34. The yeast cell of embodiment 33, wherein the expression construct is transiently contained in the yeast cell.

35. The yeast cell of embodiment 33, wherein the expression construct is stably contained in the yeast cell.

37. The yeast cell of embodiments 33-35, wherein the yeast cell comprises a cell from a *Pichia pastoris* strain, a cell from a *Pichia methanolica* strain, a cell from a *Pichia angusta* strain, a cell from a *Schizosaccharomyces pombe* strain, a cell from a *Saccharomyces cerevisiae* strain or a cell from a *Yarrowia lipolytica* strain.

38. The yeast cell of embodiments 33-35, wherein the yeast cell is a cell from a *Pichia pastoris* strain.

39. A yeast cell comprising a yeast expression construct of embodiments 18-32.

40. The yeast cell of embodiment 39, wherein the expression construct is transiently contained in the yeast cell.

41. The yeast cell of embodiment 39, wherein the expression construct is stably contained in the yeast cell.

42. The yeast cell of embodiments 39-41, wherein the yeast cell comprises a cell from a *Pichia pastoris* strain, a cell from a *Pichia methanolica* strain, a cell from a *Pichia angusta* strain, a cell from a *Schizosaccharomyces pombe* strain, a cell from a *Saccharomyces cerevisiae* strain or a cell from a *Yarrowia lipolytica* strain.

43. The yeast cell of embodiments 39-41, wherein the yeast cell is a cell from a *Pichia pastoris* strain.

44. A method of producing an enterokinase, the method comprising the step of expressing an enterokinase using a yeast cell of embodiments 33-43

45. The method of embodiment 44, wherein the method further comprises purifying the enterokinase.

46. A method of cleaving a recombinant polypeptide, the method comprising the step of contacting a recombinant polypeptide including a cleavage site of SEQ ID NO: 1 with an enterokinase, wherein the enterokinase is produced by a method of embodiment 44 or 45, wherein contacting the recombinant polypeptide with the enterokinase results in a specific cleavage of SEQ ID NO: 1.

47. A method of preparing a recombinant polypeptide, the method comprising the step of contacting a recombinant polypeptide including a cleavage site of SEQ ID NO: 1 with an enterokinase, wherein the enterokinase is produced by a method of embodiment 44 or 45, wherein contacting the recombinant polypeptide with the enterokinase results in a specific cleavage of SEQ ID NO: 1.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the methods of expression EK using a yeast expression system as disclosed herein.

Example 1

Synthesis of a Polynucleotide Molecule Encoding EK

A polynucleotide molecule SEQ ID NO: 4 is synthesized using standard chemical procedures (BlueHeron Biotechnology, Bothell, Wash.). For example, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/EK. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). A similar synthesis strategy is used to make a polynucleotide molecule SEQ ID NO: 6, nucleotide variants of SEQ ID NO: 4 or SEQ ID NO: 6, and truncated variants of SEQ ID NO: 4 or SEQ ID NO: 6.

If desired, an expression optimized polynucleotide molecule based on SEQ ID NO: 2, SEQ ID NO: 4, or SEQ ID NO: 6 is synthesized in order to improve expression in yeast cell. The polynucleotide molecule encoding the EK is modified to 1) contain synonymous codons typically present in native polynucleotide molecules of a yeast strain of choice; 2) contain a G+C content that more closely matches the average G+C content of native polynucleotide molecules found in a yeast strain of choice; 3) reduce polymononucleotide regions found within the polynucleotide molecule; and/or 4) eliminate internal regulatory or structural sites found within the polynucleotide molecule, see, e.g., Lance E. Steward et al., *Optimizing Expression of Active Botulinum Toxin Type E*, International Patent Publication WO 2006/011966 (Feb. 2, 2006); Lance E. Steward et al., Optimizing Expression of Active Botulinum Toxin Type A, International Patent Publication WO 2006/017749 (Feb. 16, 2006), each entirely incorporated by reference. Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/EK. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). A similar synthesis strategy is used to make a polynucleotide molecule that is nucleotide variants of SEQ ID NO: 4 or SEQ ID NO: 6, or truncated variants of SEQ ID NO: 4 or SEQ ID NO: 6.

Example 2

Construction and Expression of pPpT4Alpha/EK

To construct a yeast expression construct comprising polynucleotide molecule encoding EK as disclosed herein, a pJ201/rEK construct containing SEQ ID NO: 4 was digested with XhoI and NotI to excise the SEQ ID NO: 4 insert. The resulting restriction fragment was purified by the QIAQUICK® Gel Extraction Kit (QIAGEN, Inc., Valencia, Calif.), and the SEQ ID NO: 4 fragment was subcloned into the pPpT4Alpha_S vector (Ingenza, Ltd., Midlothian, UK) that had been digested with restriction endonucleases XhoI and NotI. The pPpT4Alpha_S vector includes an Alpha Factor secretion signal sequence, a portion of a AOX1 promoter, AOD and AOX1 transcript termination sequences, and an open reading frame for ZEOCIN™. The fragment and vector were ligated using T4 DNA ligase protocol to yield pPpT4Alpha/rEK and an aliquot of this ligation mixture was transformed by a standard electroporation protocol into electro-competent NEB10 cells (New England Biolabs, Inc., Ipswich, Mass.). The transformed cells were plated onto 1.5% Luria-Bertani Lennox agar plates (pH 7.0) containing 25 µg/mL of ZEOCIN™, and placed in a 37° C. incubator for overnight growth. Candidate expression constructs were selected as ZEOCINT™-resistant colonies. Resistant colonies were subsequently grown, harvested and plasmid DNA isolated using standard procedures and candidate expression constructs were screened by restriction digestion using XhoI and NotI, XbaI, or NdeI to determine the presence and orientation of the correct insert fragment. Cultures containing the desired pPpT4Alpha/rEK expression construct were grown, harvested and plasmid DNA isolated using standard procedures and candidate expression constructs were sequenced to verify that the correct expression construct was made. This cloning strategy yielded a yeast expression construct comprising SEQ ID NO: 4. A similar strategy is used to make a pPpT4Alpha/EK expression construct including SEQ ID NO: 6, a nucleotide variant of SEQ ID NO: 4 or SEQ ID NO: 6, or a truncated variant of SEQ ID NO: 4 or SEQ ID NO: 6. Alternatively, a polynucleotide molecule of SEQ ID NO: 4, SEQ ID NO: 4, a nucleotide variant of SEQ ID NO: 4 or SEQ ID NO: 6, or truncated variant of SEQ ID NO: 4 or SEQ ID NO: 6 is synthesized as described in Example 1.

To construct a yeast cell line expressing an enterokinase encoded by SEQ ID NO: 4, DNA from the pPpT4Alpha/rEK expression construct was polymerase chain reaction (PCR) amplified using a AOX forward primer of SEQ ID NO: 8 and a PUC reverse primer of SEQ ID NO: 9 to produce a linear integration cassette. The first five base pairs of the AOX forward primer contain a Bg/II site that is not identical to the pPpT4Alpha/EK DNA sequence. The AOX forward primer binds after the region which is part of the AOX1 Promoter. Although the full length AOX1 gene is not present on the linear integration cassette, the entire full length AOX1 gene is reconstituted upon integration with the *P. pastoris* chromosome. The resulting linearized expression construct was transformed into an appropriate *P. pastoris* Mut$^S$ strain CBS7435 using an electroporation method. The transformation mixture was plated on 1.5% Yeast, Peptone, Dextrose, Sorbitol (YPDS) agar plates (pH 7.5) containing 100 µg/mL, 250 µg/mL, or 500 µg/mL of ZEOCIN™ and placed in a 28-30° C. incubator for 1-3 days. Selection of transformants integrating the pPpT4Alpha/EK fragment at the 5' AOX1 locus is determined by colony resistance to ZEOCIN™. Sixty-two recombinant colonies were selected from the various YPDS plates containing the different concentrations of ZEOCIN™, and inoculated into Yeast, Peptone, and Dextrose (YPD) broth containing 100 µg/mL ZEOCIN™. The isolated yeast cell lines grew as expected in the YPD broth containing ZEOCIN™, indicating that the strains were Zeocin resistant and contained the integrated pPpT4Alpha/EK cassette. Aliquots of the YPD cultures containing isolated cell yeast lines were placed in vials having 1 mL YPD broth containing 10% (v/v) Glycerol to create established yeast cell lines, and the vials were stored at −80° C. A similar strategy is used to make a yeast cell line expressing an enterokinase of SEQ ID NO: 6, a nucleotide variant of SEQ ID NO: 4 or SEQ ID NO: 6, or a truncated variant of SEQ ID NO: 4 or SEQ ID NO: 6.

To further verify the presence of the integrated pPpT4Alpha/E cassette and determine the relative EK gene copy number in each isolated yeast cell line, PCR analysis was carried out on the 62 isolated cell lines. One mL was removed from the YPD cultures discussed above was lysed and genomic DNA isolate using standard procedures. The isolated genomic DNA was PCR amplified for 29 cycles using an EK forward primer of SEQ ID NO: 10 and an EK reverse primer of SEQ ID NO: 11 to produce a 250-bp product from the EK gene. After completion of the amplification, the reaction mix was resolved on a 0.8% agarose gel containing a polynucleotide stain alongside a 0.1 Kb to 10 Kb size 2-log DNA Ladder. These experiments confirmed that for 61 cell lines tested, the expected 250-bp EK fragment was generated. PCR amplification was repeated using the same genomic DNA preparations but with only 18 cycles in order to estimate relative copy number between the strains. Although a relatively low level of variation was observed, four cell lines exhibited a higher gene copy number relative to the others.

Example 3

Assays for Enterokinase Activity

To test for the presence, quality and quantity of the expressed enterokinase, cell lines containing an integrated pPpT4Alpha/EK cassette were assayed using a liquid colorimetric enterokinase (EK) assay, SDS-PAGE, Western blot, and ELISA. To induce expression of enterokinase from the integrated pPpT4Alpha/EK cassette, an aliquot from each established yeast cell line was used to inoculate 100 mL baffled shake flasks containing 10 mL of defined growth media including 1.34% (w/v) Yeast Nitrogen Base (YNB), 200 mM phosphate buffer, $4 \times 10^{-5}$% (w/v) Biotin, and 1% (v/v) glycerol. The inoculates were grown at about 28-30° C. in a shaker incubator (250 rpm) for about 60-65 hours. To induce enterokinase expression, 1 mL of primary induction media including 1.34% (w/v) Yeast Nitrogen Base (YNB), 200 mM phosphate buffer, $4 \times 10^{-5}$% (w/v) Biotin, and 5% (v/v) methanol is added to the culture flasks. The cells were cultured at about 28-30° C. in a shaker incubator (250 rpm) for about 8-10 hours. The cultures were charged with a 100 µL of methanol, cultured for about 16-18 hours and an additional 100 µL of methanol was added to the media every 24 hours with the final charge added about 72-74 hours post induction. In order to compare data obtained from shake flask samples, the benchmark strain B18 (a *P. pastoris* CBS7435 Mut$^S$ pPpT4Alpha/EK-HIS expression construct that produces a His-tagged enterokinase) was set up in duplicate shake flasks alongside the integrated strains.

To determine enzymatic activity of the expressed enterokinase, samples were taken during the course of the culture induction and assayed for enterokinase activity using a liquid colorimetric enterokinase activity assay. A test aliquot of media was taken from the yeast cultures described above at 0 hour, 24, hours, 48 hours, 72 hours and 96 hours post-induction. Test aliquots were added to a tube and centrifuged twice at 14,000 rpm to ensure removal of cells. An aliquot of the prepared media sample was then added to a reaction mixture containing the 1 mM of colorimetric peptide substrate N-carbobenzyloxy-Lys-ThioBenzyl ester (Z-Lys-SBZL; Bachem, AG, Bubendorf, CH) in the presence of 5,5'Dithio-bis(2-nitrobenzoic acid) (DTNB). The cleavage reaction initiated colorless to yellow color change from and the initial rate was measured on the plate reader in kinetic mode at an absorbance of 405 nm. The enzyme concentration was adjusted to ensure sample dilutions were within the linear range of the assay (0-100 mOD/min). Samples were assayed in triplicate alongside negative and positive controls.

Following the enterokinase activity assay results of all strains, the a liquid colorimetric enterokinase activity assay was repeated using four established yeast cell lines with the highest enterokinase activity, referred to as YCL-48, YCL-49, YCL-98 and YCL-99, and the two cell lines with the lowest enterokinase activity, referred to as YCL-40 and YCL-88. All samples were assayed in triplicate using a single batch of substrates. FIG. 1 shows the mean enterokinase activity for each yeast cell line against time post induction. The error bars indicate the 95% confidence interval between the triplicate shake flask values. From the data, YCL-49 had the highest enterokinase activity and YCL-88 had the lowest activity.

To determine identity and quality of the expressed enterokinase, samples from the 96-98 hours post induction time point of YCL-40, YCL-48, YCL-49, YCL-88, YCL-98 and YCL-99 were taken and analyzed using SDS-PAGE and Western blot analysis. Samples were added to 2×SDS Sample Buffer and separated by MOPS polyacrylamide gel electrophoresis using 10-20% Bis-Tris precast polyacrylamide gels (Expedeon, Inc, San Diego, Calif.) under denaturing, reducing conditions. For SDS-PAGE analysis, the gels were stained with Coomassie Brilliant Blue to reveal the protein banding patterns. For Western blot analysis, the separated polypeptides were transferred to nitrocellulose and stained with a polyclonal α-enterokinase antibody. The enterokinase polypeptide was clearly visible on the SDS-PAGE and Western blots as a single band at approximately 38 kDa. The electrophoretic migration indicates that the enterokinase has undergone post-translational modification. In addition, the lack of any detectable spurious bands indicated the high quality of the expressed enterokinase of the yeast cell lines with the integrated pPpT4Alpha/EK cassette.

To determine concentration of the expressed enterokinase, samples from the 96-98 hours post induction time point of YCL-49, YCL-88, and YCL-98 were taken and analyzed using a sandwich Enzyme-linked immunosorbant assay (ELISA). A series of dilutions were prepared form the test samples and were assayed in triplicate alongside defined concentrations from a commercially available recombinant enterokinase standard (EMD Biosciences-Novagen, Madison, Wis.). The standard curve produced from the dilution series of the commercial standard enabled quantification of the YCL-49 and YCL-88 samples. The ELISA results were used to calculate the level of EK material present in the supernatant of whole broth samples obtained following shake flask growth and expression of the integrated strains (Table 3).

TABLE 3

ELISA Analysis

| Sample | Enterokinase Concentration |
|---|---|
| B18 | 1.0 µg/mL |
| YCL-49 | 2.6 µg/mL |
| YCL-88 | 2.9 µg/mL |
| YCL-98 | 2.2 µg/mL |

The above described analyses indicated that several established yeast cells lines expressed a high quality, enzymatically-active enterokinase from the integrated pPpT4Alpha/EK cassette.

Example 4

Construction and Expression of pPICZ A/EK-myc-His

To construct a yeast expression construct comprising polynucleotide molecule encoding EK as disclosed herein, restriction endonuclease sites suitable for cloning an operably linked nucleic acid molecule into a pPIC A vector (Invitrogen, Inc, Carlsbad, Calif.) are incorporated into the 5'- and 3' ends of SEQ ID NO: 4 using standard DNA synthesis procedures. This construct is digested with restriction enzymes that 1) excise SEQ ID NO: 4 encoding an enterokinase; and 2) enable this insert to be operably-linked to a pPIC A vector. This insert is subcloned using a T4 DNA ligase procedure into a pPIC A vector that is digested with appropriate restriction endonucleases to yield pPIC A/BoNT/E-myc-His. The ligation mixture is transformed into chemically competent *E. coli* DH5a cells (Invitrogen, Inc, Carlsbad, Calif.) using a heat shock method, plated on 1.5% low salt Luria-Bertani agar plates (pH 7.5) containing 25 μg/mL of ZEOCIN™, and placed in a 37° C. incubator for overnight growth. Bacteria containing expression constructs are identified as ZEOCIN™ resistant colonies. Candidate constructs are isolated using an alkaline lysis plasmid mini-preparation procedure and analyzed by restriction endonuclease digest mapping to determine the presence and orientation of the insert. This cloning strategy yields a yeast expression construct encoding an enterokinase operably linked to carboxy-terminal c-myc and polyhistidine binding peptides. A similar strategy is used to make a pPIC A/EK expression construct including SEQ ID NO: 6, a nucleotide variant of SEQ ID NO: 4 or SEQ ID NO: 6, or a truncated variant of SEQ ID NO: 4 or SEQ ID NO: 6.

To construct a yeast cell line expressing an enterokinase, pPICZ A/EK-myc-His is digested with a suitable restriction endonuclease (i.e., SacI, PmeI or BstXI) and the resulting linearized expression construct is transformed into an appropriate *P. pastoris* $Mut^S$ strain KM71H using an electroporation method. The transformation mixture is plated on 1.5% YPDS agar plates (pH 7.5) containing 100 μg/mL of ZEOCIN™ and placed in a 28-30° C. incubator for 1-3 days of growth. Selection of transformants integrating the pPICZ A/EK-myc-His at the 5' AOX1 locus is determined by colony resistance to ZEOCIN™. Cell lines integrating a pPICZ A/EK-myc-His construct are then tested for enterokinase expression. Isolated colonies from test cell lines that have integrated pPICZ A/EK-myc-His are used to inoculate 1.0 L baffled flasks containing 100 mL of MGYH media and grown at about 28-30° C. in a shaker incubator (250 rpm) until the culture reaches an $OD_{600}$=2-6 (approximately 16-18 hours). Cells are harvested by centrifugation (3,000×g at 22° C. for 5 minutes). To induce expression, the cell pellet is resuspended in 15 mL of MMH media and 100% methanol is added to a final concentration of 0.5%. Cultures are grown at about 28-30° C. in a shaker incubator (250 rpm) for six days. Additional 100% methanol is added to the culture every 24 hours to a final concentration of 0.5%. A 1.0 mL test aliquot is taken from the culture every 24 hours starting at time zero and ending at time 144 hours. Cells are harvested from the aliquots by microcentrifugation to pellet the cells and lysed using three freeze-thaw rounds consisting of −80° C. for 5 minutes, then 37° C. for 5 minutes. Lysis samples are added to 2×SDS Sample Buffer (Invitrogen, Inc, Carlsbad, Calif.) and expression from established cell lines is measured by SDS-PAGE and Western blot analysis (as described in Example 3). The *P. pastoris* $Mut^S$ KM71H cell line showing the highest expression level of enterokinase is selected for large-scale expression using commercial fermentation procedures. Procedures for large-scale expression are as outlined above except the culture volume is approximately 2.5 L MGYH media grown in a 5 L BioFlo 3000 fermentor and concentrations of all reagents will be proportionally increased for this volume. For greater details on all procedures described in this example, see EasySelect™ *Pichia* Expression Kit, version G, A Manual of Methods for Expression of Recombinant Proteins Using pPICZ and pPICZa in *Pichia pastoris,* 122701, 25-0172 (Invitrogen, Inc, Carlsbad, Calif.). A similar strategy is used to make a yeast cell line expressing an enterokinase of SEQ ID NO: 6, a nucleotide variant of SEQ ID NO: 4 or SEQ ID NO: 6, or a truncated variant of SEQ ID NO: 4 or SEQ ID NO: 6.

Example 5

Construction and Expression of pMET/EK-V5-His

To construct a yeast expression construct comprising polynucleotide molecule encoding EK as disclosed herein, restriction endonuclease sites suitable for cloning an operably linked nucleic acid molecule into a pMET vector (Invitrogen, Inc, Carlsbad, Calif.) are incorporated into the 5'- and 3' ends of SEQ ID NO: 4 using standard DNA synthesis procedures. This construct is digested with restriction enzymes that 1) excise SEQ ID NO: 4 encoding an enterokinase; and 2) enable this insert to be operably-linked to a pMET vector. This insert is subcloned using a T4 DNA ligase procedure into a pMET vector that is digested with appropriate restriction endonucleases to yield pMET/BoNT/E-V5-His. The ligation mixture is transformed into chemically competent *E. coli* DH5a cells (Invitrogen, Inc, Carlsbad, Calif.) using a heat shock method, plated on 1.5% low salt Luria-Bertani agar plates (pH 7.5) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy yields a yeast expression construct encoding an enterokinase operably linked to carboxy-terminal V5 and polyhistidine binding peptides. A similar strategy is used to make a pMET/EK expression construct including SEQ ID NO: 6, a nucleotide variant of SEQ ID NO: 4 or SEQ ID NO: 6, or a truncated variant of SEQ ID NO: 4 or SEQ ID NO: 6.

To construct a yeast cell line expressing an enterokinase, pMET/BoNT/E-V5-His is digested with a suitable restriction endonuclease (i.e., ApaI, AscI, FseI, PacI, KpnI or PstI) and the resulting linearized expression construct is transformed into an appropriate *P. methanolica* $Mut^S$ strain PMAD16 using an electroporation method. The transformation mixture is plated on 1.5% MD agar plates (pH 7.5) lacking adenine and grown in a 28-30° C. incubator for 3-4 days. Selection of transformants integrating the pMET/EK-V5-His is determined by colony growth on adenine-deficient media. Ade+ cell lines integrating a pMET/EK-V5-His construct are tested for enterokinase expression using a small-scale expression test. Isolated Ade+ colonies from test cell lines that have integrated pMET/EK-V5-His are used to inoculate 15 mL of BMDY media and cells are grown at about 28-30° C. in a shaker incubator (250 rpm) until the culture reaches an $OD_{600}$=2-10 (approximately 16-18 hours). Cells are harvested by centrifugation (1,500×g at 22° C. for 5 minutes). To induce expression, cell pellets are resuspended in 5 mL of BMMY media and cultures are grown at about 28-30° C. in a shaker incubator (250 rpm). After 24 hours, a 500 µL aliquot is removed, methanol is added to a final concentration of 0.5% and the cultures are grown at about 28-30° C. in a shaker incubator (250 rpm). A 500 µL aliquot is removed and additional methanol is added to a final concentration of 0.5% to the culture every 24 hours for 3-5 days. Harvested cells are centrifuged (1,500×g at 4° C. for 5 minutes), washed once in water and cell pellets stored at −80° C. until needed. To detect expression of the induced enterokinase, the cell pellets of each time point are lysed using an acid-washed glass bead method. Lysis samples are added to 2×SDS Sample Buffer (Invitrogen, Inc, Carlsbad, Calif.) and expression from established cell lines is measured by SDS-PAGE and Western blot analysis (as described in Example 3). The *P. methanolica* Mut$^S$ PMAD16 cell line showing the highest expression level of enterokinase is selected for large-scale expression using commercial fermentation procedures. Procedures for large-scale expression are as outlined above except the culture volume is approximately 2.5 L BMDY/BMMY media grown in a 5 L BioFlo 3000 fermentor and concentrations of all reagents will be proportionally increased for this volume. For greater details on all procedures described in this example, see *P. methanolica* Expression Kit, version C, A Manual of Methods for Expression of Recombinant Proteins in *Pichia methanolica*, 062101, 25-0288 (Invitrogen, Inc, Carlsbad, Calif.). A similar strategy is used to make a yeast cell line expressing an enterokinase of SEQ ID NO: 6, a nucleotide variant of SEQ ID NO: 4 or SEQ ID NO: 6, or a truncated variant of SEQ ID NO: 4 or SEQ ID NO: 6.

Example 6

Construction and Expression of pYES2/EK-V5-His

To construct a yeast expression construct comprising polynucleotide molecule encoding EK as disclosed herein, restriction endonuclease sites suitable for cloning an operably linked nucleic acid molecule into a pYES2 vector (Invitrogen, Inc, Carlsbad, Calif.) are incorporated into the 5' and 3' ends of SEQ ID NO: 4 using standard DNA synthesis procedures. This construct is digested with restriction enzymes that 1) excise SEQ ID NO: 4 encoding an enterokinase; and 2) enable this insert to be operably-linked to a pYES2 vector. This insert is subcloned using a T4 DNA ligase procedure into a pYES2 vector that is digested with appropriate restriction endonucleases to yield pYES2/EK-V5-His. The ligation mixture is transformed into chemically competent *E. coli* DH5α cells (Invitrogen, Inc, Carlsbad, Calif.) using a heat shock method, plated on 1.5% low salt Luria-Bertani agar plates (pH 7.5) containing 100 µg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy yields a yeast expression construct encoding an enterokinase operably linked to carboxy-terminal V5 and polyhistidine binding peptides. A similar strategy is used to make a pYES2/EK expression construct including SEQ ID NO: 6, a nucleotide variant of SEQ ID NO: 4 or SEQ ID NO: 6, or a truncated variant of SEQ ID NO: 4 or SEQ ID NO: 6.

To construct a yeast cell line expressing an enterokinase, pYES2/EK-V5-His is transformed into competent *S. cerevisiae* strain INVSc1 using a Lithium-based transformation method. The transformation mixture is plated on 2% SC minimal media agar plates (pH 7.5) containing 2% glucose, that either have 0.01% uracil or lack uracil and placed in a 28-30° C. incubator for 1-3 days of growth. Selection of transformants containing pYES2/EK-V5-His is determined by colony growth only on plates containing uracil. Cells containing a pYES2/EK-V5-His construct are tested forenterokinase expression using a small-scale expression test. Isolated colonies from test cells containing pYES2/EK-V5-His are used to inoculate 50 mL tubes containing 15 mL of SC media containing 2% glucose and 0.01% uracil and grown overnight at about 28-30° C. in a shaker incubator (250 rpm). The $OD_{600}$ of overnight cultures are determined and aliquoted to obtain a cell concentration of $OD_{600}$ of 0.4 in a 50 mL volume. These aliquots are centrifuged (1,500×g at 22° C. for 5 minutes) and the resulting cell pellet resuspended in SC media containing 20% galactose and 10% raffinose. Cells are grown at about 28-30° C. in a shaker incubator (250 rpm) and 5 mL aliquots are taken at 0 hours, 4 hours, 8 hours, 12 hours, 16 hours and 24 hours and $OD_{600}$ concentrations are determined for each sample. Harvested cells are centrifuged (1,500×g at 4° C. for 5 minutes), washed once in water and cell pellets stored at −80° C. until needed. To detect expression of the induced BoNT/E-V5-His, the cell pellets of each time point are lysed using an acid-washed glass bead method. Lysis samples are added to 2×SDS Sample Buffer (Invitrogen, Inc, Carlsbad, Calif.) and expression from established cell lines is measured by SDS-PAGE and Western blot analysis (as described in Example 3). The induction conditions resulting in the highest expression level of enterokinase are selected for large-scale expression using commercial fermentation procedures. Procedures for large-scale expression are as outlined above except the culture volume is approximately 2.5 L SC media grown in a 5 L BioFlo 3000 fermentor and concentrations of all reagents will be proportionally increased for this volume. For greater details on all procedures described in this example, see pYES2/CT, pYES3/CT, and pYC2/CT Yeast Expression Vectors with C-terminal Tags and Auxotrophic Selection Markers, version E, 25-0304, Jan. 27, 2003 (Invitrogen, Inc, Carlsbad, Calif.). A similar strategy is used to make a yeast cell line expressing an enterokinase of SEQ ID NO: 6, a nucleotide variant of SEQ ID NO: 4 or SEQ ID NO: 6, or a truncated variant of SEQ ID NO: 4 or SEQ ID NO: 6.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. An isolated polynucleotide molecule comprising the nucleotide sequence of SEQ ID NO: 4 or SEQ ID NO: 6.

2. The isolated polynucleotide molecule according to claim 1, wherein the isolated polynucleotide molecule further comprises a yeast expression construct.

3. A yeast expression construct comprising a yeast expression vector operably-linked to a polynucleotide comprising the nucleotide sequence of SEQ ID NO: 4.

4. The yeast expression construct according to claim 3, wherein the yeast expression construct further comprises a polynucleotide encoding an alpha factor operably-linked to the polynucleotide comprising the nucleotide sequence of SEQ ID NO: 4.

5. The yeast expression construct according to claim 4, wherein the nucleotide sequence of the polynucleotide encoding an alpha factor operably-linked to the polynucleotide comprising the nucleotide sequence of SEQ ID NO: 4 is SEQ ID NO: 6.

6. A yeast cell transformed with a yeast expression construct comprising a polynucleotide having the nucleotide sequence of SEQ ID NO: 4 or SEQ ID NO: 6.

7. The yeast cell according to claim 6, wherein the expression construct is extra-chromosomal in the yeast cell.

8. The yeast cell according to claim 6, wherein the expression construct is stably integrated into the chromosome of the yeast cell.

9. The yeast cell according to claim 6, wherein the yeast cell is a *Pichia pastoris*, a *Pichia methanolica*, a *Pichia anqusta*, a *Schizosaccharomyces pombe*, a *Saccharomyces cerevisiae*, or a *Yarrowia lipolytica* cell.

10. The yeast cell according to claim 6, wherein the yeast cell is a *Pichia pastoris* cell.

11. A method of producing an enterokinase, the method comprising the step of culturing a yeast cell transformed with a yeast expression construct comprising a polynucleotide haying the nucleotide sequence of SEQ ID NO: 4 or SEQ ID NO: 6 to thereby produce an enterokinase encoded by the nucleotide sequence of SEQ ID NO: 4 or SEQ ID NO: 6.

12. The method according to claim 11, wherein the yeast cell is a *Pichia pastoris*, a *Pichia methanolica*, a *Pichia anqusta*, a *Schizosaccharomyces pombe*, a *Saccharomyces cerevisiae*, or a *Yarrowia lipolytica* cell.

13. The method according to claim 11, wherein the yeast cell is a *Pichia pastoris* cell.

14. The method according to claim 11, wherein the method further comprises purifying the enterokinase encoded by the nucleotide sequence of SEQ ID NO: 4 or SEQ ID NO: 6.

* * * * *